(12) United States Patent
Ito et al.

(10) Patent No.: US 12,037,417 B2
(45) Date of Patent: *Jul. 16, 2024

(54) SITE-SPECIFIC RADIOISOTOPE-LABELED ANTIBODY USING IGG-BINDING PEPTIDE

(71) Applicant: Kagoshima University, Kagoshima (JP)

(72) Inventors: Yuji Ito, Kagoshima (JP); Yoshinari Shoyama, Tokyo (JP); Akio Hayashi, Tokyo (JP); Norihito Nakata, Tokyo (JP)

(73) Assignee: Kagoshima University, Kagoshima (JP)

( * ) Notice: Subject to any disclaimer, the term of this patent is extended or adjusted under 35 U.S.C. 154(b) by 1418 days.

This patent is subject to a terminal disclaimer.

(21) Appl. No.: 16/309,272

(22) PCT Filed: Jun. 12, 2017

(86) PCT No.: PCT/JP2017/021558
§ 371 (c)(1),
(2) Date: Dec. 12, 2018

(87) PCT Pub. No.: WO2017/217347
PCT Pub. Date: Dec. 21, 2017

(65) Prior Publication Data
US 2020/0181196 A1    Jun. 11, 2020

(30) Foreign Application Priority Data

Jun. 13, 2016 (JP) .................... 2016-117395
Nov. 22, 2016 (JP) .................... 2016-227025

(51) Int. Cl.
| | | |
|---|---|---|
| *C07K 7/08* | (2006.01) | |
| *C07K 7/64* | (2006.01) | |
| *G01N 33/534* | (2006.01) | |
| *G01N 33/574* | (2006.01) | |

(52) U.S. Cl.
CPC ............... *C07K 7/08* (2013.01); *C07K 7/64* (2013.01); *G01N 33/534* (2013.01); *G01N 33/574* (2013.01)

(58) Field of Classification Search
None
See application file for complete search history.

(56) References Cited

U.S. PATENT DOCUMENTS

| | | | |
|---|---|---|---|
| 5,256,395 A | 10/1993 | Barbet et al. | |
| 8,372,950 B2 | 2/2013 | Ito | |
| 9,593,147 B2 | 3/2017 | Ito | |
| 10,227,383 B2* | 3/2019 | Ito .................. | C07K 19/00 |
| 11,186,613 B2 | 11/2021 | Ito et al. | |
| 2002/0006379 A1* | 1/2002 | Hansen .............. | B82Y 5/00 |
| | | | 424/1.49 |
| 2003/0235534 A1 | 12/2003 | Griffiths et al. | |
| 2011/0218157 A1 | 9/2011 | Bodie | |
| 2011/0306554 A1 | 12/2011 | Masaki | |
| 2014/0274790 A1 | 9/2014 | Ito | |
| 2018/0141976 A1 | 5/2018 | Ito | |

FOREIGN PATENT DOCUMENTS

| | | |
|---|---|---|
| EP | 1 757 311 A2 | 2/2007 |
| JP | 63-159327 A | 7/1988 |
| JP | 2002-518460 A | 6/2002 |
| JP | 2005-532343 A | 10/2005 |
| WO | WO 99/66951 A2 | 12/1999 |
| WO | WO 2013/027796 A1 | 2/2013 |
| WO | WO 2016/186206 A1 | 11/2016 |

OTHER PUBLICATIONS

Publication date for Journal of Peptide Science v22 issue S2 34th European peptide symposium, retrieved from https://onlinelibrary.wiley.com/toc/10991387/2016/22/S2 on Nov. 29, 2022, 4 pages (Year: 2022).*
Ito et al. ('Specific chemical modification of human antibodies by a reagent based on FC-specific affinity peptide' Journal of Peptide Science v22 issue S2 34th European peptide symposium, 2016, total of 126 pages) (Year: 2016).*
International Search Report dated Sep. 5, 2017, in PCT/JP2017/021558.
Axup et al., "Synthesis of site-specific antibody-drug conjugates using unnatural amino acids," PNAS, Oct. 2, 2012, 109(40):16101-16106.
Bejot et al., "Aminooxy-functionalized DOTA for radiolabeling of oxidized antibodies: evaluation of site-specific $^{111}$In-labeled trastuzumab," Journal of Labelled Compounds and Radiopharmaceuticals, Jul. 27, 2012, 55:346-353.
Bernardes et al., "Site-specific chemical modification of antibody fragments using traceless cleavable linkers," Nature Protocols, 2013, 8(11):2079-2089.
Boyraz et al., "Review, Trastuzumab emtansine (T-DM1) for HER2-positive breast cancer," Current Medical Research and Opinion, 2013, 29(4):405-414.
Denler et al,. "Transglutaminase-Based Chemo-Enzymatic Conjugation Approach Yields Homogeneous Antibody-Drug Conjugates," Bioconjugate Chemistry, 2014, 25:569-578.
Hashida et al., "More Useful Maleimide Compounds for the Conjugation of Fab' to Horseradish Peroxidase through Thiol Groups in the Hinge," Journal of Applied Biochemistry, 1984, 6:56-63.
Hermanson et al., "3. Biotinylation Reagents Containing Discrete PEG Linkers," Bioconjugate Techniques, 3$^{rd}$ Ed., 2013, 726-739.

(Continued)

*Primary Examiner* — Ronald T Niebauer
(74) *Attorney, Agent, or Firm* — Foley & Lardner LLP

(57) ABSTRACT

The present invention relates to an IgG-binding peptide comprising a ligand capable of binding to a radioactive metal nuclide, an IgG-binding peptide labeled with a radioactive metal nuclide, a conjugate of the IgG-binding peptide and IgG, and a radionuclide imaging agent or a diagnostic agent for cancer comprising the IgG-binding peptide or the conjugate, etc.

7 Claims, 11 Drawing Sheets
Specification includes a Sequence Listing.

(56) References Cited

OTHER PUBLICATIONS

Imagawa et al., "Characteristics and Evaluation of Antibody-Horseradish Peroxidase Conjugates Prepared by Using a Maleimide Compound, Glutaraldehyde, and Periodate," Journal of Applied Biochemistry, 1982, 4:41-57.

Jeger et al., "Site-Specific and Stoichiometric Modification of Antibodies by Bacterial Transglutaminase," Angewandte Chemie, Intl. Ed., 2010, 49:9995-9997.

Phillips et al., "Targeting HER2-Positive Breast Cancer with Trastuzumab-DM1, an Antibody-Cytotoxic Drug Conjugate," Cancer Res., Nov. 15, 2008, 68(22):9280-9290.

Rodwell et al., "Site-specific covalent modification of monoclonal antibodies: In vitro and in vivo evaluations," PNAS USA, Apr. 1986, 83:2632-2636.

Shen et al., "Conjugation site modulates the in vivo stability and therapeutic activity of antibody-drug conjugates," Nature Biotechnology, Feb. 2012, 30(2):184-189.

Tian et al., "A general approach to site-specific antibody drug conjugates," PNAS, Feb. 4, 2014, 111(5):1766-1771.

Zhou et al., "Site-Specific Antibody-Drug Conjugation through Glycoengineering," Bioconjugate Chemistry, Feb. 17, 2014, 25:510-520.

Zimmerman et al., "Production of Site-Specific Antibody-Drug Conjugates Using Optimized Non-Natural Amino Acids in a Cell-Free Expression System," Bioconjugate Chemistry, Jan. 17, 2014, 25:351-361.

Leaver-Fay et al., "Computationally Designed Bispecific Antibodies Using Negative State Repertoires," Structure, Apr. 5, 2016, 24(4):641-651.

Office Action dated Nov. 23, 2021 in KR 10-2018-7035255.

Office Action dated Feb. 7, 2022 in CN 201780025871.0.

U.S. Appl. No. 17/284,309, filed Apr. 9, 2021, Ito et al.

U.S. Appl. No. 17/199,255, filed Mar. 11, 2021, Yuji Ito.

Office Action dated Aug. 7, 2023 in U.S. Appl. No. 17/199,255.

* cited by examiner

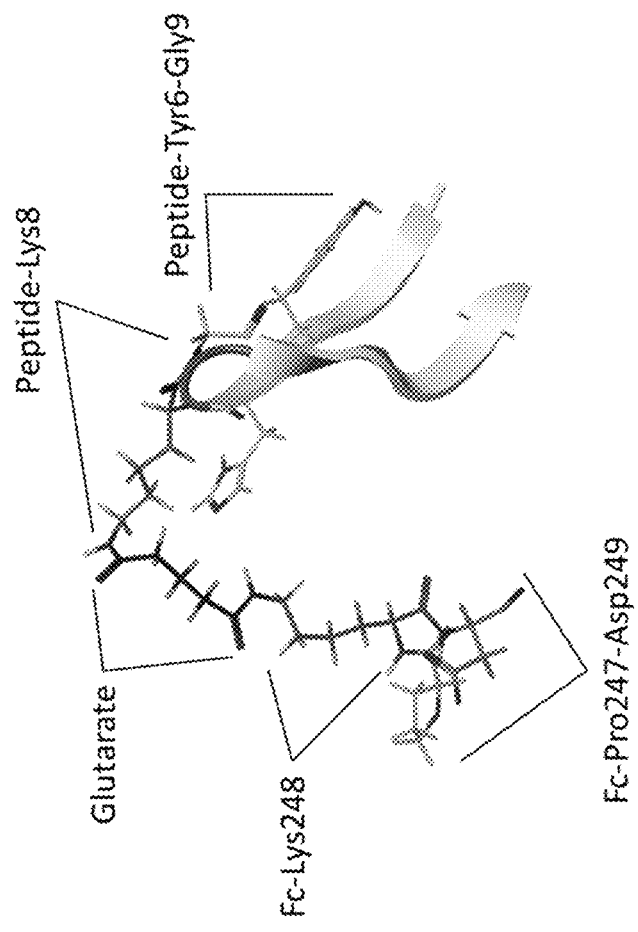
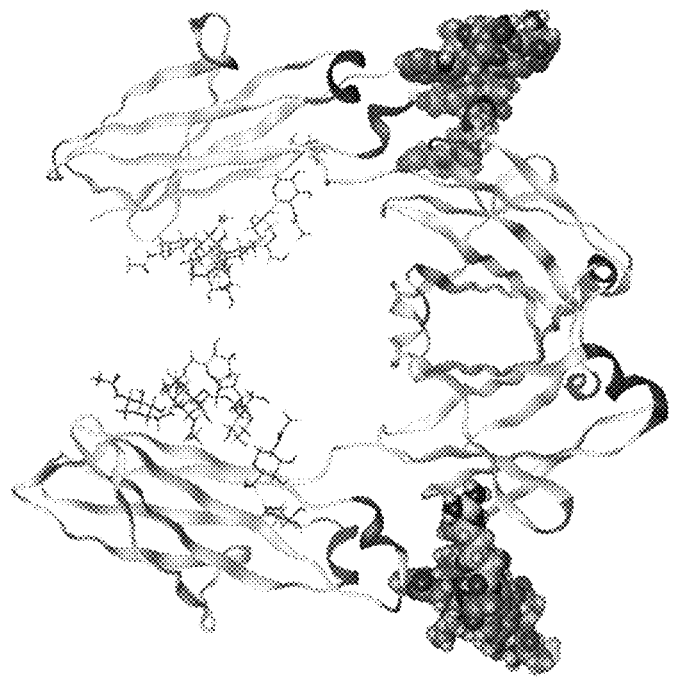
Fig. 1

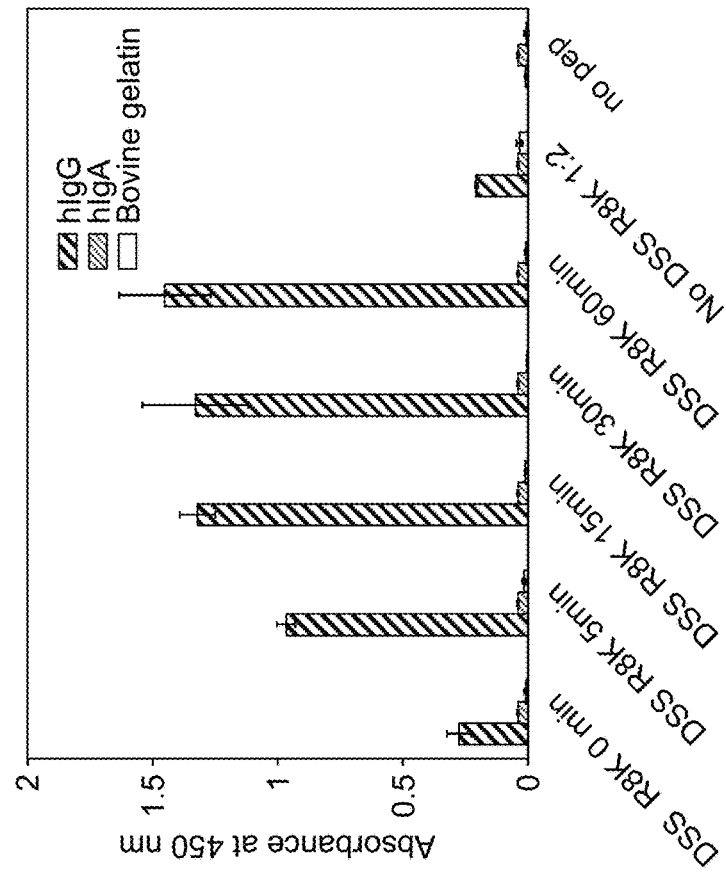
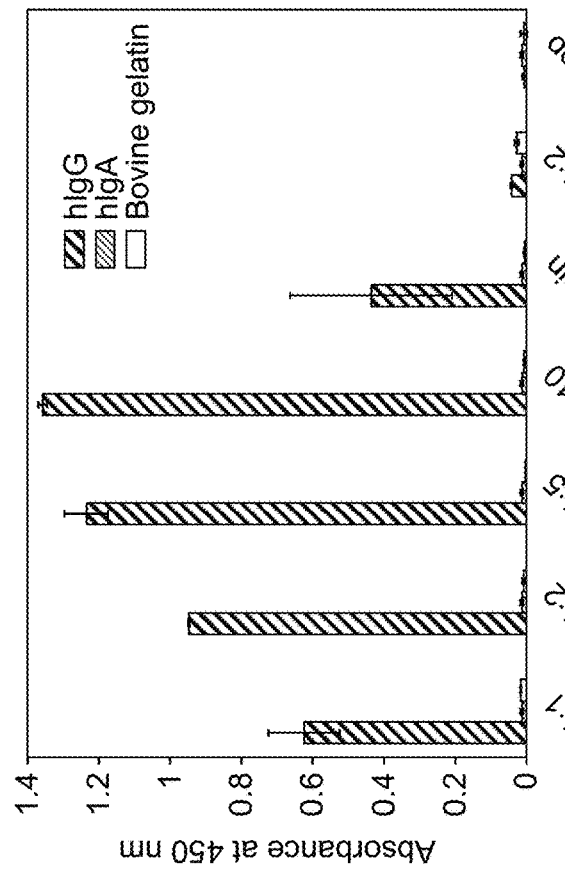
Fig. 3

SEQUENCE LISTING

<160> NUMBER OF SEQ ID NOS: 48

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 1

```
Asp Cys Ala Tyr His Xaa Gly Glu Leu Val Trp Cys Thr
1               5                   10
```

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 2

```
Gly Pro Asp Cys Ala Tyr His Xaa Gly Glu Leu Val Trp Cys Thr Phe
1               5                   10                  15

His
```

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 3

```
Arg Cys Ala Tyr His Xaa Gly Glu Leu Val Trp Cys Ser
1               5                   10
```

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 4

```
Gly Pro Arg Cys Ala Tyr His Xaa Gly Glu Leu Val Trp Cys Ser Phe
1               5                   10                  15

His
```

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic acid residue, a glutamic acid residue, 2-aminosuberic acid, or
diaminopropionic acid

<400> SEQUENCE: 5

Ser Pro Asp Cys Ala Tyr His Xaa Gly Glu Leu Val Trp Cys Thr Phe
1               5                   10                  15

His

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 6

Gly Asp Asp Cys Ala Tyr His Xaa Gly Glu Leu Val Trp Cys Thr Phe
1               5                   10                  15

His

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 7

Gly Pro Ser Cys Ala Tyr His Xaa Gly Glu Leu Val Trp Cys Thr Phe
1               5                   10                  15

His

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 8

Gly Pro Asp Cys Ala Tyr His Xaa Gly Glu Leu Val Trp Cys Ser Phe
1               5                   10                  15

His

<210> SEQ ID NO 9
<211> LENGTH: 17

```
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 9

Gly Pro Asp Cys Ala Tyr His Xaa Gly Glu Leu Val Trp Cys Thr His
1               5                   10                  15

His

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 10

Gly Pro Asp Cys Ala Tyr His Xaa Gly Glu Leu Val Trp Cys Thr Phe
1               5                   10                  15

Tyr

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 11

Ser Pro Asp Cys Ala Tyr His Xaa Gly Glu Leu Val Trp Cys Thr Phe
1               5                   10                  15

Tyr

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 12
```

Ser Asp Asp Cys Ala Tyr His Xaa Gly Glu Leu Val Trp Cys Thr Phe
1               5                   10                  15

Tyr

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 13

Arg Gly Asn Cys Ala Tyr His Xaa Gly Gln Leu Val Trp Cys Thr Tyr
1               5                   10                  15

His

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 14

Asp Cys Thr Tyr His Xaa Gly Asn Leu Val Trp Cys Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 15

Asp Cys Ala Tyr His Xaa Gly Asn Leu Val Trp Cys Thr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)

```
<223> OTHER INFORMATION: Lysine residue, a cysteine residue, an aspartic
      acid residue, a glutamic acid residue, 2-aminosuberic acid, or
      diaminopropionic acid

<400> SEQUENCE: 16

Asp Cys Thr Tyr His Xaa Gly Glu Leu Val Trp Cys Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 17

Asp Cys Ala Trp His Xaa Gly Glu Leu Val Trp Cys Thr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 18

Asp Cys Thr Tyr Thr Xaa Gly Asn Leu Val Trp Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 19

Asp Cys Ala Tyr Thr Xaa Gly Asn Leu Val Trp Cys Thr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
```

```
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 20

Asp Cys Ser Tyr Thr Xaa Gly Asn Leu Val Trp Cys Thr
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 21

Asp Cys Thr Trp Thr Xaa Gly Asn Leu Val Trp Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 22

Asp Cys Thr Tyr His Xaa Gly Asn Leu Val Trp Cys Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 23

Asp Cys Thr Tyr Arg Xaa Gly Asn Leu Val Trp Cys Thr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
```

```
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 24

Asp Cys Thr Tyr Ser Xaa Gly Asn Leu Val Trp Cys Thr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 25

Asp Cys Thr Tyr Thr Xaa Gly Asn Leu Val Trp Cys Thr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 26

Asp Cys Thr Tyr Thr Xaa Gly Glu Leu Val Trp Cys Thr
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 27

Asp Cys Thr Tyr Thr Xaa Gly Arg Leu Val Trp Cys Thr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
```

```
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 28

Asp Cys Thr Tyr Thr Xaa Gly Asp Leu Val Trp Cys Thr
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 29

Asp Cys Thr Tyr Thr Xaa Gly Asn Leu Ile Trp Cys Thr
1               5                   10

<210> SEQ ID NO 30
<211> LENGTH: 110
<212> TYPE: PRT
<213> ORGANISM: Homo sapiens

<400> SEQUENCE: 30

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (2)..(2)
<223> OTHER INFORMATION: Homocysteine
<220> FEATURE:
<221> NAME/KEY: MOD_RES
<222> LOCATION: (16)..(16)
<223> OTHER INFORMATION: Homocysteine

<400> SEQUENCE: 31
```

Gly Xaa Asp Cys Ala Tyr His Arg Gly Glu Leu Val Trp Cys Thr Xaa
1               5                   10                  15

His

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid

<400> SEQUENCE: 32

Gly Pro Asp Cys Ala Tyr His Xaa Gly Glu Leu Val Trp Cys Thr Phe
1               5                   10                  15

His

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide

<400> SEQUENCE: 33

Asp Cys Ala Tyr His Arg Gly Glu Leu Val Trp Cys Thr
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      IgG-binding peptide

<400> SEQUENCE: 34

Asp Cys Ala Tyr His Lys Gly Glu Leu Val Trp Cys Thr
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (8)..(8)
<223> OTHER INFORMATION: Lys(DSG)

<400> SEQUENCE: 35

Arg Gly Asn Cys Ala Tyr His Lys Gly Gln Leu Val Trp Cys Thr Tyr
1               5                   10                  15

His

<210> SEQ ID NO 36
<211> LENGTH: 17

```
<212> TYPE: PRT
<213> ORGANISM: Artificial Sequence
<220> FEATURE:
<223> OTHER INFORMATION: Description of Artificial Sequence: Synthetic
      IgG-binding peptide
<220> FEATURE:
<221> NAME/KEY: MOD_RES
<222> LOCATION: (2)..(2)
<223> OTHER INFORMATION: Homocysteine
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid
<220> FEATURE:
<221> NAME/KEY: MOD_RES
<222> LOCATION: (16)..(16)
<223> OTHER INFORMATION: Homocysteine

<400> SEQUENCE: 36

Gly Xaa Asp Cys Ala Tyr His Xaa Gly Glu Leu Val Trp Cys Thr Xaa
1               5                   10                  15

His

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      IgG-binding peptide

<400> SEQUENCE: 37

Gly Pro Asp Cys Ala Tyr His Lys Gly Glu Leu Val Trp Cys Thr Phe
1               5                   10                  15

His

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid residue other than cysteine
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (5)..(6)
<223> OTHER INFORMATION: Any amino acid residue other than cysteine
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid
<220> FEATURE:
<221> NAME/KEY: MOD_RES
<222> LOCATION: (10)..(10)
<223> OTHER INFORMATION: Glutamic acid residue, a glutamine residue, or
      an asparagine residue
<220> FEATURE:
<221> NAME/KEY: MOD_RES
<222> LOCATION: (15)..(17)
<223> OTHER INFORMATION: Any amino acid residue other than cysteine
<220> FEATURE:
```

```
<221> NAME/KEY: MISC_FEATURE
<222> LOCATION: (15)..(17)
<223> OTHER INFORMATION: This region may encompass 1-3 residues

<400> SEQUENCE: 38

Xaa Xaa Xaa Cys Xaa Xaa His Xaa Gly Xaa Leu Val Trp Cys Xaa Xaa
1               5                   10                  15

Xaa

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Alanine residue, a serine residue or a
      threonine residue
<220> FEATURE:
<221> NAME/KEY: MOD_RES
<222> LOCATION: (4)..(4)
<223> OTHER INFORMATION: Tryptophan residue or a tyrosine residue
<220> FEATURE:
<221> NAME/KEY: MOD_RES
<222> LOCATION: (5)..(5)
<223> OTHER INFORMATION: Histidine residue, an arginine residue, a
      serine residue or a threonine residue
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid
<220> FEATURE:
<221> NAME/KEY: MOD_RES
<222> LOCATION: (8)..(8)
<223> OTHER INFORMATION: Glutamic acid residue, a glutamine residue, an
      asparagine residue, an arginine residue, or an aspartic acid
      residue
<220> FEATURE:
<221> NAME/KEY: MOD_RES
<222> LOCATION: (10)..(10)
<223> OTHER INFORMATION: Isoleucine residue or a valine residue

<400> SEQUENCE: 39

Asp Cys Xaa Xaa Xaa Xaa Gly Xaa Leu Xaa Trp Cys Thr
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid residue other than cysteine
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (5)..(5)
<223> OTHER INFORMATION: Any amino acid residue other than cysteine
<220> FEATURE:
<221> NAME/KEY: MOD_RES
<222> LOCATION: (8)..(8)
<223> OTHER INFORMATION: Lysine residue, a cysteine residue, an aspartic
```

```
       acid residue, a glutamic acid residue, 2-aminosuberic acid, or
       diaminopropionic acid
<220> FEATURE:
<221> NAME/KEY: MOD_RES
<222> LOCATION: (15)..(17)
<223> OTHER INFORMATION: Any amino acid residue other than cysteine
<220> FEATURE:
<221> NAME/KEY: MISC_FEATURE
<222> LOCATION: (15)..(17)
<223> OTHER INFORMATION: This region may encompass 1-3 residues

<400> SEQUENCE: 40

Xaa Xaa Xaa Cys Xaa Tyr His Xaa Gly Asn Leu Val Trp Cys Xaa Xaa
1               5                   10                  15

Xaa

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (1)..(3)
<223> OTHER INFORMATION: Any amino acid residue other than cysteine
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (6)..(6)
<223> OTHER INFORMATION: Any amino acid residue other than cysteine
<220> FEATURE:
<221> NAME/KEY: MOD_RES
<222> LOCATION: (8)..(8)
<223> OTHER INFORMATION: Lysine residue, a cysteine residue, an aspartic
       acid residue, a glutamic acid residue, 2-aminosuberic acid, or
       diaminopropionic acid
<220> FEATURE:
<221> NAME/KEY: MOD_RES
<222> LOCATION: (15)..(17)
<223> OTHER INFORMATION: Any amino acid residue other than cysteine
<220> FEATURE:
<221> NAME/KEY: MISC_FEATURE
<222> LOCATION: (15)..(17)
<223> OTHER INFORMATION: This region may encompass 1-3 residues

<400> SEQUENCE: 41

Xaa Xaa Xaa Cys Ala Xaa His Xaa Gly Glu Leu Val Trp Cys Xaa Xaa
1               5                   10                  15

Xaa

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<221> NAME/KEY: MOD_RES
<222> LOCATION: (1)..(3)
<223> OTHER INFORMATION: Any amino acid residue other than cysteine
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (5)..(5)
```

```
<223> OTHER INFORMATION: Alanine residue, a serine residue or a
      threonine residue
<220> FEATURE:
<221> NAME/KEY: MOD_RES
<222> LOCATION: (6)..(6)
<223> OTHER INFORMATION: Tyrosine residue or a tryptophan residue
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid
<220> FEATURE:
<221> NAME/KEY: MOD_RES
<222> LOCATION: (10)..(10)
<223> OTHER INFORMATION: Glutamic acid residue, a glutamine residue, or
      an asparagine residue
<220> FEATURE:
<221> NAME/KEY: MOD_RES
<222> LOCATION: (15)..(17)
<223> OTHER INFORMATION: Any amino acid residue other than cysteine
<220> FEATURE:
<221> NAME/KEY: MISC_FEATURE
<222> LOCATION: (15)..(17)
<223> OTHER INFORMATION: This region may encompass 1-3 residues

<400> SEQUENCE: 42

Xaa Xaa Xaa Cys Xaa Xaa His Xaa Gly Xaa Leu Val Trp Cys Xaa Xaa
1               5                   10                  15

Xaa

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Any amino acid residue other than cysteine
<220> FEATURE:
<221> NAME/KEY: MISC_FEATURE
<222> LOCATION: (1)..(3)
<223> OTHER INFORMATION: This region may encompass 1-3 residues
<220> FEATURE:
<221> NAME/KEY: MOD_RES
<222> LOCATION: (8)..(8)
<223> OTHER INFORMATION: Lysine residue, a cysteine residue, an aspartic
      acid residue, a glutamic acid residue, 2-aminosuberic acid, or
      diaminopropionic acid
<220> FEATURE:
<221> NAME/KEY: MOD_RES
<222> LOCATION: (15)..(17)
<223> OTHER INFORMATION: Any amino acid residue other than cysteine
<220> FEATURE:
<221> NAME/KEY: MISC_FEATURE
<222> LOCATION: (15)..(17)
<223> OTHER INFORMATION: This region may encompass 1-3 residues

<400> SEQUENCE: 43

Xaa Xaa Xaa Cys Ala Tyr His Xaa Gly Glu Leu Val Trp Cys Xaa Xaa
1               5                   10                  15

Xaa

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Alanine residue or a threonine residue
<220> FEATURE:
<221> NAME/KEY: MOD_RES
<222> LOCATION: (4)..(4)
<223> OTHER INFORMATION: Tyrosine residue or a tryptophan residue
<220> FEATURE:
<221> NAME/KEY: MOD_RES
<222> LOCATION: (6)..(6)
<223> OTHER INFORMATION: Lysine residue, a cysteine residue, an aspartic
      acid residue, a glutamic acid residue, 2-aminosuberic acid, or
      diaminopropionic acid
<220> FEATURE:
<221> NAME/KEY: MOD_RES
<222> LOCATION: (8)..(8)
<223> OTHER INFORMATION: Glutamic acid residue, a glutamine residue, or
      an asparagine residue

<400> SEQUENCE: 44

Asp Cys Xaa Xaa His Xaa Gly Xaa Leu Val Trp Cys Thr
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Pro Asp Cys Ala Tyr His Arg Gly Glu Leu Val Trp Cys Thr Phe
1               5                   10                  15

His

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Asp Asp Cys Ala Tyr His Lys Gly Glu Leu Val Trp Cys Thr Phe
1               5                   10                  15

His

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(DSG-OH)

<400> SEQUENCE: 47

Gly Asp Asp Cys Ala Tyr His Lys Gly Glu Leu Val Trp Cys Thr Phe
1               5                   10                  15

His

<210> SEQ ID NO 48
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(DSS-OH)

<400> SEQUENCE: 48

Gly Asp Asp Cys Ala Tyr His Lys Gly Glu Leu Val Trp Cys Thr Phe
1               5                   10                  15

His
```

SITE-SPECIFIC RADIOISOTOPE-LABELED ANTIBODY USING IGG-BINDING PEPTIDE

CROSS-REFERENCE TO RELATED APPLICATIONS

This application is the U.S. National Stage of PCT/JP2017/021558, filed Jun. 12, 2017, which claims priority to JP 2016-117395, filed Jun. 13, 2016, and JP 2016-227025, filed Nov. 22, 2016.

The instant application contains a Sequence Listing which has been submitted in ASCII format via EFS-WEB and is hereby incorporated by reference in its entirety. Said ASCII copy, created on Jun. 15, 2020, is named 081356-0541 SL.txt and is 26,371 bytes.

TECHNICAL FIELD

The present invention relates to an IgG-binding peptide comprising a ligand capable of binding to a radioactive metal nuclide, an IgG-binding peptide labeled with a radioactive metal nuclide, a conjugate of the IgG-binding peptide and IgG, and a radionuclide imaging agent or a diagnostic agent for cancer comprising the IgG-binding peptide or the conjugate, etc.

BACKGROUND ART

Antibodies have conventionally been often utilized in the detection of target molecules in various research and development activities, and are also of great industrial importance as detection reagents or diagnostic drugs. The antibodies have also received attention as drugs for the treatment of diseases because of their specificity for target molecules.

In order to impart a function to antibodies, labeling with radioisotopes is practiced via iodation or addition of a chelating compound (Non Patent Literature 1), etc. These modifications have been typically performed so far via a lysine amino group, a cysteine thiol group, and an activated carboxyl group, etc. contained in antibodies. These modifications are specific for the functional groups, but are not site-specific. Therefore, these approaches have the problems of, for example, reduction in the activity of antibodies due to the modification or the like of the antigen-binding sites of the antibodies, and difficult control of the number of compounds to be bound.

In order to overcome these problems, antibody modification has been practiced using antibodies having a particular site-specifically introduced functional group. For example, modification at a particular site is achieved by introducing a non-natural amino acid (Non Patent Literatures 2 to 4) or free cysteine (Non Patent Literatures 5 and 6) to the particular site by genetic manipulation. Although site-specific antibody modification techniques are under development as mentioned above, these methods often require engineering antibodies themselves and are not always advantageous in light of reduction in the functions of the antibodies and high development cost in association with the engineering.

CITATION LIST

Non Patent Literature

Non Patent Literature 1: Rodwell, J. D. et al., Proceedings of the National Academy of Sciences of the United States of America, 1986, 83, pp. 2632-2636

Non Patent Literature 2: Axup, J. Y. et al., Proceedings of the National Academy of Sciences of the United States of America, 2012, 109, pp. 16101-16106

Non Patent Literature 3: Tian, F. et al., Proceedings of the National Academy of Sciences of the United States of America, 2014, 111, pp. 1766-1771

Non Patent Literature 4: Zimmerman, E. S. et al., Bioconjugate chemistry, 2014, 25, pp. 351-361

Non Patent Literature 5: Shen, B. Q. et al., Nature biotechnology, 2012, 30, pp. 184-189

Non Patent Literature 6: Bernardes, G. J. et al., Nature protocols, 2013, 8, pp. 2079-2089

SUMMARY OF INVENTION

Accordingly, there is a demand for methods that can modify antibodies specifically and conveniently.

In order to solve the problems described above, the present inventors have conducted detailed studies on the position of each amino acid in an IgG-binding peptide in a bound state and the positional relationship of each amino acid with IgG Fc, on the basis of the X-ray crystallography of a conjugate of the IgG-binding peptide and the IgG Fc. The present inventors have further found that: an IgG-binding peptide site-specifically modified with a cross-linking agent can be prepared by introducing an amino acid capable of binding to the cross-linking agent to a peptide and modifying the amino acid with the cross-linking agent; and IgG can be modified using this IgG-binding peptide site-specifically modified with a cross-linking agent. Moreover, the present inventor has found that a conjugate of an IgG-binding peptide labeled with a radioactive metal nuclide and IgG can be used as a diagnostic agent for cancer. On the basis of the findings, the present invention has been completed.

Therefore, the present invention encompasses the following embodiments.

(1) A peptide which comprises an amino acid sequence consisting of 13 to 17 amino acid residues represented by the following formula I:

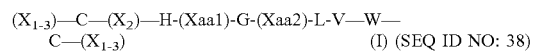

wherein each X is independently any amino acid residue other than cysteine,

C is a cysteine residue,

H is a histidine residue,

Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue, a glutamine residue, or an asparagine residue, L is a leucine residue, V is a valine residue, and W is a tryptophan residue, wherein the peptide is capable of binding to human IgG, and comprises a ligand capable of binding to a radioactive metal nuclide.

(2) A peptide which comprises an amino acid sequence consisting of 13 to 17 amino acid residues represented by the following formula I:

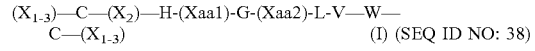

wherein each X is independently any amino acid residue other than cysteine,

C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue, a glutamine residue, or an asparagine residue,
L is a leucine residue,
V is a valine residue, and
W is a tryptophan residue,
wherein the peptide is capable of binding to human IgG, and is labeled with a radioactive metal nuclide.

(3) A peptide which comprises an amino acid sequence consisting of 13 amino acid residues represented by the following formula V:

D-C-(Xaa2)-(Xaa3)-(Xaa4)-(Xaa1)-G-(Xaa5)-L-(Xaa6)-W—C-T     (V) (SEQ ID NO: 39)

wherein
D is an aspartic acid residue,
C is a cysteine residue,
G is a glycine residue,
L is a leucine residue,
W is a tryptophan residue,
T is a threonine residue,
Xaa1 is a lysine residue, a cysteine residue, an aspartic acid residue, a glutamic acid residue, 2-aminosuberic acid, or diaminopropionic acid,
Xaa2 is an alanine residue, a serine residue or a threonine residue,
Xaa3 is a tryptophan residue or a tyrosine residue,
Xaa4 is a histidine residue, an arginine residue, a serine residue or a threonine residue,
Xaa5 is a glutamic acid residue, a glutamine residue, an asparagine residue, an arginine residue, or an aspartic acid residue, and
Xaa6 is an isoleucine residue or a valine residue,
wherein the peptide is capable of binding to human IgG, and wherein a radioactive metal nuclide is bound to the peptide via a ligand.

(4) A conjugate of the peptide and IgG, wherein the conjugate is formed through the cross-linking reaction of the above described peptide modified with the cross-linking agent with the IgG.

(5) A radionuclide imaging agent or a diagnostic agent for cancer comprising the peptide according to (2) or (3), or the conjugate according to (4), wherein a radioactive metal nuclide is bound to the peptide.

(6) A method for determining the presence or absence of cancer in a subject, comprising the steps of:
reacting a sample obtained from the subject with the peptide according to (2) or (3), or the conjugate according to (4), wherein a radioactive metal nuclide is bound to the peptide;
measuring a level or presence of radioactivity derived from the radioactive metal nuclide in the sample; and
determining the presence or absence of cancer in the subject on the basis of the level or presence of radioactivity.

(7) A method for determining the presence or absence of cancer in a subject, comprising the steps of:
administering the peptide according to (2) or (3), or the conjugate according to (4) to the subject, wherein a radioactive metal nuclide is bound to the peptide;
measuring a level or presence of radioactivity derived from the radioactive metal nuclide in the subject; and
determining the presence or absence of cancer in the subject on the basis of the level or presence of radioactivity.

This description includes all or part of the contents disclosed in Japanese Patent Applications No. 2016-117395, and No. 2016-227025, to which the present application claims the priority.

The IgG-binding peptide of the present invention can be easily bound with a radioactive metal nuclide. Therefore, IgG can be labeled specifically and conveniently with the radioactive metal nuclide by using the IgG-binding peptide of the present invention. Furthermore, the IgG-binding peptide of the present invention eliminates the need of altering the sequence of the antibody molecule and therefore does not cause reduction in the functions of the antibody molecule associated with genetic engineering. Moreover, the IgG-binding peptide of the present invention eliminates the need of reaction of directly labeling IgG with a radioactive metal nuclide, which has conventionally been required, and does not cause reduction in the functions of the antibody caused by the reaction.

BRIEF DESCRIPTION OF DRAWINGS

FIG. 1(A) shows the structure of a conjugate of an IgG-binding peptide (C35A-3/15: DCAYHRGELVWCT (SEQ ID NO: 33)) and human IgG Fc. The IgG-binding peptide is depicted as a space-filling model, the IgG Fc is depicted as a ribbon model, and the sugar chain of the Fc is depicted as a wire model. FIG. 1(B) shows a model of the cross-linked structure between an IgG-binding peptide (C35A-3/15(R8K): DCAYHKGELVWCT (SEQ ID NO: 34)) modified with DSG and IgG Fc. The main chain of the peptide is depicted as a ribbon model. Peptide-Lys8 represents the lysine residue at position 6 of C35A-3/15(R8K), and peptide-Tyr6-Gly9 represents the tyrosine residue at position 4 to the glycine residue at position 7 of C35A-3/15(R8K). Fc-Lys248 represents Lys248 of Fc according to the EU numbering, and Fc-Pro247-Asp249 represents Pro247 to Asp249 of Fc according to the EU numbering.

FIG. 3 shows results of study for reaction molar ratio (A) and reaction time (B) by ELISA for the reaction between a labeled IgG-binding peptide and IgG. DSS R8K 0 min represents that Tris-HCl (pH 7.0) was added to a labeling IgG-binding peptide at a 10-fold molar ratio to IgG, and the mixture was added to wells after blocking of a NHS group. No DSS R8K represents that a DSS-unbound biotinylated IgG-binding (R8K) peptide was used. no pep represents a control without the addition of the peptide.

FIG. 4(A) shows results of measuring the reactivity of an IgG-binding peptide modified with DSS. FIG. 4(B) shows results of measuring the reactivity of an IgG-binding peptide modified with DSG.

DESCRIPTION OF EMBODIMENTS

<IgG-Binding Peptide>

Figure 2:
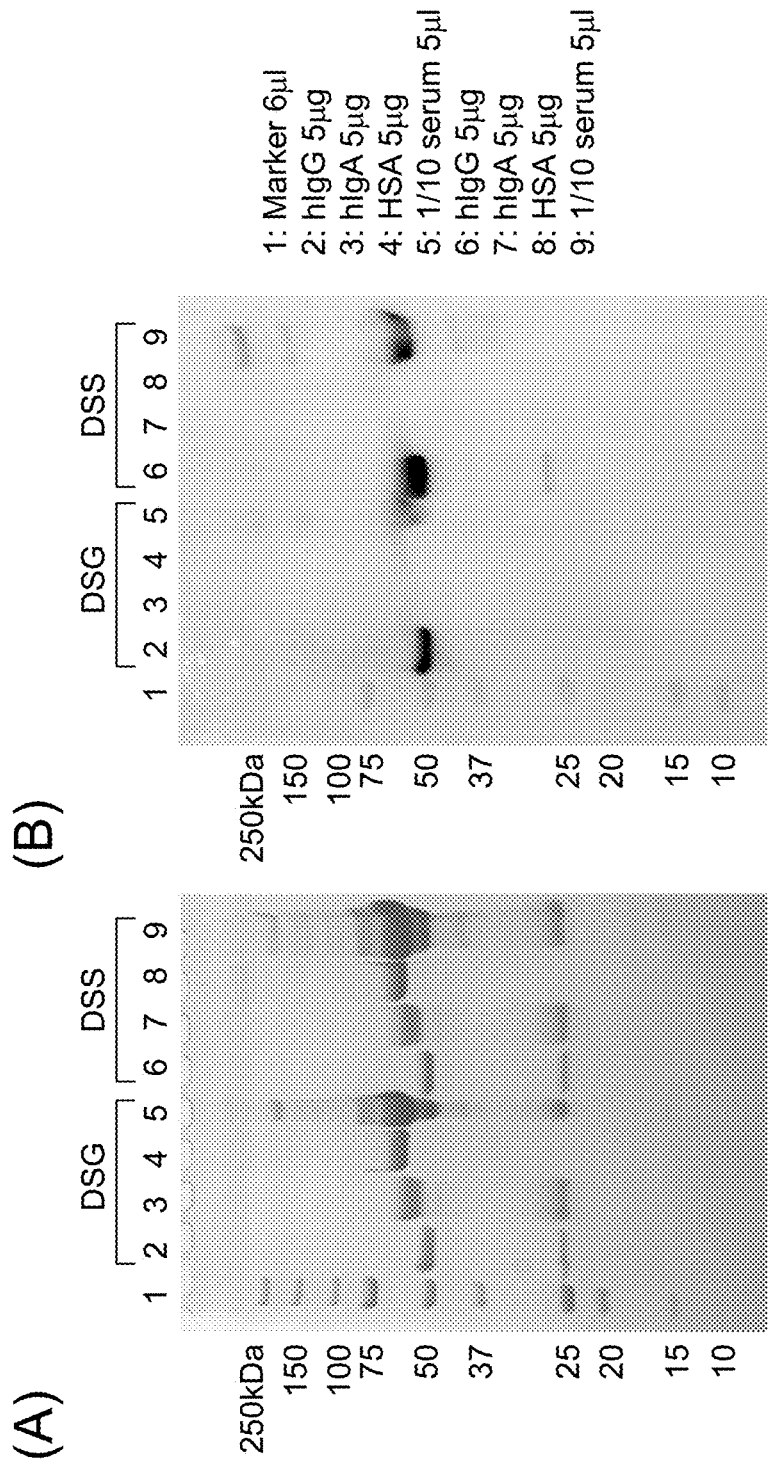
FIG. 2 shows results of SDS-PAGE (A) and Western blot (B) of mixtures of labeled IgG-binding peptides and various proteins. In the figure, DSG represents that an IgG-binding peptides reacted with DSG (disuccinimidyl glutarate) were subjected, and DSS represents that an IgG-binding peptides reacted with DSS (disuccinimidyl suberate) were subjected. In the figure, hIgG represents human IgG, hIgA represents human IgA, and HSA represents human serum albumin.

In one aspect, the present invention relates to an IgG-binding peptide comprising a ligand capable of binding to a radioactive metal nuclide. The position of the ligand in the IgG-binding peptide is not particularly limited. For example, the ligand can be linked to the N terminus or the C terminus, preferably the N terminus, of the IgG-binding peptide. The method for linking the ligand to the peptide is well known to those skilled in the art. In the case of linking the ligand to, for example, the N terminus of the IgG-binding peptide, a reactive group such as N-hydroxysuccinimide ester (NHS), an isothiocyano group (ITC), sulfonic acid chloride, carboxylic acid chloride, ethylene oxide, alkyl chloride, an aldehyde group, or carboxylic anhydride can be attached to the ligand and reacted with the N-terminal amino group of the IgG-binding peptide. Alternatively, the IgG-binding peptide comprising such a ligand may be directly synthesized by a well-known synthesis method or the like.

Examples of the ligand capable of binding to a radioactive metal nuclide that may be contained in the IgG-binding peptide of the present invention include, but are not limited to, chelating agents, for example, diethylenetriaminepentaacetic acid (DTPA), deferoxamine, 1,4,7,10-tetraazacyclododecane-1,4,7,10-tetraacetic acid (DOTA), 1,4,7-triazacyclononane-1,4,7-triacetic acid (NOTA), ethylenediaminetetraacetic acid (EDTA), ethylenediaminediacetic acid, triethylenetetraminehexaacetic acid (TTHA), 1,4,8,11-tetraazacyclotetradecane-1,4,8,11-tetraacetic acid (TETA), dipyridoxyl diphosphate (DPDP), TPPS$_4$, ethylenebishydroxyphenylglycine (EHPG), hexamethylenediaminetetraacetic acid, dimethylphosphinomethane (DMPE), methylenediphosphoric acid, dimercaptosuccinic acid (DMPA), and derivatives thereof.

In one embodiment, a radioactive metal nuclide is bound to the IgG-binding peptide. Examples of the radioactive metal nuclide include $^{111}$In (indium), $^{89}$Zr (zirconium), $^{67/68}$Ga (gallium), $^{99m}$Tc (technetium), and $^{64}$Cu (copper), preferably $^{111}$In and $^{89}$Zr. The radioactive metal nuclide to be bound to the IgG-binding peptide can be selected depending on the purposes of the IgG-binding peptide and a conjugate of the IgG-binding peptide and IgG mentioned later. For example, $^{111}$In, $^{89}$Zr, $^{64}$Cu, $^{67/68}$Ga, and $^{99m}$Tc can be used for the detection or diagnosis of cancer. For example, $^{89}$Zr and $^{64}$Cu can be used for PET (positron emission tomography), and $^{111}$In and $^{99m}$Tc can be used for SPECT (single photon emission computed tomography).

The radioactive metal nuclide may be bound directly to the IgG-binding peptide, but is preferably bound to the IgG-binding peptide via a ligand such as the chelating agent. Those skilled in the art can appropriately select a preferred combination of the radioactive metal nuclide and the ligand (see e.g., Hiroshi Sakurai and Yo Yokoyama ed., Housha Yakuhingaku Gairon (General Introduction to Radiation Medicine Science in English). Examples thereof include: $^{111}$In and DTPA; $^{89}$Zr and deferoxamine; $^{64}$Cu and DOTA or NOTA; $^{99m}$Tc and dimethylphosphinomethane (DMPE), DTPA, methylenediphosphoric acid, dimercaptosuccinic acid (DMPA), dithiosemicarbazone, or diaminoethanediol; and $^{67/68}$Ga and deferoxamine or a DTPA derivative etc., preferably $^{111}$In and DTPA; $^{89}$Zr and deferoxamine; and $^{64}$Cu and DOTA or NOTA, more preferably $^{111}$In and DTPA; and $^{89}$Zr and deferoxamine, further preferably $^{111}$In and DTPA.

The IgG binding peptide of the present invention is described in detail below.

The "IgG" used in the present specification refers to IgG of a mammal, for example, a primate (such as a human and a chimpanzee), a laboratory animal (such as a rat, a mouse, and a rabbit), a livestock animal (such as a pig, cattle, a horse, sheep, and a goat), or a pet animal (such as a dog and a cat), preferably human IgG (IgG1, IgG2, IgG3 or IgG4). In the present specification, the IgG is more preferably human IgG1, IgG2, or IgG4, or rabbit IgG, particularly preferably human IgG1, IgG2, or IgG4.

In one aspect, the present invention relates to a peptide which comprises an amino acid sequence consisting of 13 to 17 amino acid residues represented by the following formula I and is capable of binding to human IgG:

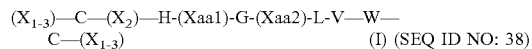

wherein each X is independently any amino acid residue other than cysteine,
C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue, a glutamine residue, or an asparagine residue,
L is a leucine residue,
V is a valine residue, and
W is a tryptophan residue.

In the above formula, the term "$X_{1-3}$" at the N terminus or the C terminus means 1 to 3 consecutive independently selected arbitrary amino acid residues X other than cysteine (C or Cys). The constituting amino acid residues are the same or different residues and preferably consist of a sequence in all of the 3 residues are different from one another. Likewise, $X_2$ means two consecutive independently selected arbitrary amino acid residues X other than cysteine (C or Cys). The constituting amino acid residues are the same or different residues and preferably consist of a sequence in which the two consecutive amino acid residues are different residues.

The two cysteine residues in the formula I can form a disulfide bond to form a cyclic peptide. The peptide of the formula I usually has a disulfide bond formed between the two cysteine residues on outer sides (other than Xaa1, when Xaa 1 is cysteine). Alternatively, in the peptide of the formula I, sulfide groups in the two cysteine residues on the outer sides may be linked via a linker represented by the following formula:

[Formula 1]

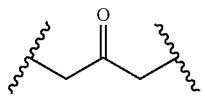

In the above formula, the broken line moieties mean binding moieties to the sulfide groups. The linker is more stable against reduction reaction or the like than usual disulfide bonds. Therefore, this linker may be preferably used when using radioactive metal nuclides which may destabilize disulfide bond such as zirconium.

This peptide can be prepared by a method comprising the step of mixing a peptide containing two or more, preferably two cysteine residues with a compound represented by the following formula:

[Formula 2]

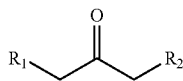

wherein $R_1$ and $R_2$ are each independently any halogen atom to obtain a peptide in which sulfide groups in the two or more, preferably two cysteine residues are linked via a linker represented by the following formula:

[Formula 3]

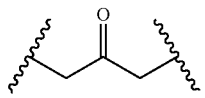

In the above formula, the broken line moieties mean binding moieties to the sulfide groups.

In the compound, $R_1$ and $R_2$ are each selected from the group consisting of preferably F, Cl, Br, and I, more preferably Cl, Br, and I. $R_1$ and $R_2$ are preferably the same. More preferably, both of $R_1$ and $R_2$ are Cl.

Conditions for the mixing step in this method are not particularly limited as long as the conditions result in linking reaction between the cysteine residues of the peptide. The reaction can be performed, for example, by mixing the peptide and the compound at room temperature (such as approximately 15° C. to 30° C.) in an appropriate buffer, for example, a buffer solution containing guanidium chloride. The mixing step may be performed by the addition of a catalyst that accelerates the linking reaction in an appropriate amount, if necessary.

The mixing ratio between the peptide and the compound in the mixing step of this method is not particularly limited. The molar ratio between the peptide and the compound can be, for example, 1:0.2 to 1:10, preferably 1:0.5 to 1:5 or 1:1 to 1:2.

The mixing time (reaction time) in the mixing step is not limited as long as the mixing time results in the linking reaction between the cysteine residues of the peptide. The mixing time can be set to, for example, 1 minute to 5 hours, preferably 10 minutes to 2 hours or 15 minutes to 1 hour.

This method may further comprise, if necessary, the step of purifying the peptide having linked cysteine residues by separating impurities, for example, unreacted peptides and compounds, from the mixture after the step described above. This step can be performed by a method known in the art, for example, chromatography such as gel filtration chromatography, ion-exchange column chromatography, affinity chromatography, reverse-phase column chromatography, or HPLC.

Peptides represented by the formula I' and the formula I" are given below, wherein the amino acid residues X in the amino acid sequence of the peptide of the formula I are defined in more detail.

Specifically, the peptide represented by the formula I' comprises an amino acid sequence consisting of 13 to 17 amino acid residues represented by

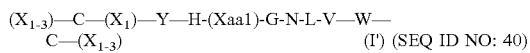

(I') (SEQ ID NO: 40)

wherein each X is independently any amino acid residue other than cysteine,
C is a cysteine residue,
Y is a tyrosine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
N is an asparagine residue,
L is a leucine residue,
V is a valine residue, and
W is a tryptophan residue.

The peptide represented by the formula I" comprises an amino acid sequence consisting of 13 to 17 amino acid residues represented by

(I") (SEQ ID NO: 41)

wherein each X is independently any amino acid residue other than cysteine,
C is a cysteine residue,
A is an alanine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
E is a glutamic acid residue,
L is a leucine residue,
V is a valine residue, and
W is a tryptophan residue.

Also, a peptide represented by the formula II is given below, wherein the amino acid residues X in the amino acid sequence of the peptide of the formula I are defined in more detail.

Specifically, the peptide represented by the formula II comprises an amino acid sequence consisting of 13 to 17 amino acid residues represented by (X$_{1-3}$)—C-(Xaa3)-(Xaa4)-H-(Xaa1)-G-(Xaa2)-L-V—W—C—(X$_{1-3}$)  (II) (SEQ ID NO: 42)

wherein each X is independently any amino acid residue other than cysteine,
C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue, a glutamine residue, or an asparagine residue,
L is a leucine residue,
V is a valine residue,
W is a tryptophan residue,
Xaa3 is an alanine residue, a serine residue or a threonine residue, and
Xaa4 is a tyrosine residue or a tryptophan residue.

In the amino acid sequences of the peptides of the formula I', the formula I" and the formula II described above, when the peptide is 17 amino acid residues, amino acid residues X from 1st, 2nd, 16th, and 17th positions from the N terminus may be deleted. Such a peptide may be 13 amino acids length.

The phrase "when the peptide is 17 amino acid residues" used in the present specification is used, for the sake of convenience, to number 17 residues, which is the largest amino acid length for the peptide of formula I, from the 1st to 17th residues in order from the N terminus, etc., when the amino acid residues of the peptide are indicated by amino acid positions.

Also, a peptide represented by the formula III is shown below, wherein the amino acid residues X in the amino acid sequence of the peptide of the formula I are defined in more detail.

Specifically, the peptide represented by the formula III comprises an amino acid sequence consisting of 13 to 17 amino acid residues represented by (X$_{1-3}$)—C-A-Y—H-(Xaa1)-G-E-L-V—W—C—(X$_{1-3}$)  (III) (SEQ ID NO: 43)

wherein each X is independently any amino acid residue other than cysteine,
C is a cysteine residue,
A is an alanine residue,
Y is a tyrosine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
E is a glutamic acid residue or a glutamine residue,
L is a leucine residue,
V is a valine residue, and
W is a tryptophan residue.

In the amino acid sequence of the peptide of the formula III described above, when the peptide is 17 amino acid residues, amino acid residues X from 1st, 2nd, 16th and 17th positions from the N terminus may be deleted. Such a peptide may be 13 amino acids length.

Each of the amino acid residues other than cysteine (C), i.e., amino acid residues from the 1st to 3rd, 5th, 6th, and 15th to 17th positions from the N terminus (when the peptide is 17 amino acid residue), in the amino acid sequence of the peptide of each formula described above, is preferably selected from those described below. In this context, each capital alphabet is a single-letter code of an amino acid:
1st amino acid residue=S, G, F, R or none,
2nd amino acid residue=D, G, A, S, P, homocysteine or none,
3rd amino acid residue=S, D, T, N, E or R,
15th amino acid residue=S, T or D,
16th amino acid residue=H, G, Y, T, N, D, F, homocysteine or none,
17th amino acid residue=Y, F, H, M or none,
5th amino acid residue=A or T, and
6th amino acid residue=Y or W.

Also, a peptide represented by the formula IV is shown below, wherein the amino acid residues X in the amino acid sequence of the peptide of the formula I are defined in more detail.

Specifically, the peptide represented by the formula IV comprises an amino acid sequence consisting of 13 amino acid residues represented by D-C-(Xaa3)-(Xaa4)-H-(Xaa1)-G-(Xaa2)-L-V—W—C-T  (IV) (SEQ ID NO: 44)

wherein
D is an aspartic acid residue,
C is a cysteine residue,
H is a histidine residue,
Xaa1 is a lysine residue, a cysteine residue, an aspartic acid residue, a glutamic acid residue, 2-aminosuberic acid, or diaminopropionic acid,
G is a glycine residue,
Xaa2 is a glutamic acid residue, a glutamine residue, or an asparagine residue,
L is a leucine residue,
V is a valine residue,
W is a tryptophan residue,
T is a threonine residue,
Xaa3 is an alanine residue or a threonine residue, and
Xaa4 is a tyrosine residue or a tryptophan residue Several specific examples of the peptide of the formula I are listed below in 1) to 18), though the peptide of the formula I is not limited to them, as a matter of course:

```
                                    (SEQ ID NO: 1)
1) DCAYH(Xaa1)GELVWCT, (SEQ ID NO: 2)
2) GPDCAYH(Xaa1)GELVWCTFH, (SEQ ID NO: 3)
3) RCAYH(Xaa1)GELVWCS, (SEQ ID NO: 4)
4) GPRCAYH(Xaa1)GELVWCSFH, (SEQ ID NO: 5)
5) SPDCAYH(Xaa1)GELVWCTFH, (SEQ ID NO: 6)
6) GDDCAYH(Xaa1)GELVWCTFH, (SEQ ID NO: 7)
7) GPSCAYH(Xaa1)GELVWCTFH,
```

-continued

8) GPDCAYH(Xaa1)GELVWCSFH, (SEQ ID NO: 8)

9) GPDCAYH(Xaa1)GELVWCTHH, (SEQ ID NO: 9)

10) GPDCAYH(Xaa1)GELVWCTFY, (SEQ ID NO: 10)

11) SPDCAYH(Xaa1)GELVWCTFY, (SEQ ID NO: 11)

12) SDDCAYH(Xaa1)GELVWCTFY, (SEQ ID NO: 12)

13) RGNCAYH(Xaa1)GQLVWCTYH, (SEQ ID NO: 13)

14) G(Xaa2)DCAYH(Xaa1)GELVWCT(Xaa2)H, (SEQ ID NO: 36)

15) DCTYH(Xaa1)GNLVWCT, (SEQ ID NO: 14)

16) DCAYH(Xaa1)GNLVWCT, (SEQ ID NO: 15)

17) DCTYH(Xaa1)GELVWCT, (SEQ ID NO: 16)
and

18) DCAWH(Xaa1)GELVWCT, (SEQ ID NO: 17)

wherein Xaa1 is a lysine residue, a cysteine residue, an aspartic acid residue, a glutamic acid residue, 2-aminosuberic acid, or diaminopropionic acid, and Xaa2 is homocysteine, and preferably, the two homocysteine residues form a disulfide bond.

Preferred specific examples of the peptide of the formula I include
1) DCAYH(Xaa1)GELVWCT (SEQ ID NO: 1),
2) GPDCAYH(Xaa1)GELVWCTFH (SEQ ID NO: 2),
13) RGNCAYH(Xaa1)GQLVWCTYH (SEQ ID NO: 13), and
14) G(Xaa2)DCAYH(Xaa1)GELVWCT(Xaa2)H (SEQ ID NO: 36), and as a particularly preferable example include 2) GPDCAYH(Xaa1)GELVWCTFH (SEQ ID NO: 2), wherein Xaa1 is a lysine residue, Xaa2 is homocysteine, and preferably, the two cysteine residues and/or the two homocysteine residues form a disulfide bond.

Further, in one aspect, the IgG binding peptide of the present invention comprises, as a primary structure in the broad sense, an amino acid sequence consisting of 13 amino acid residues represented by the following formula V:

D-C-(Xaa2)-(Xaa3)-(Xaa4)-(Xaa1)-G-(Xaa5)-L-(Xaa6)-W—C-T (V) (SEQ ID NO: 39)

wherein
D is an aspartic acid residue,
C is a cysteine residue,
G is a glycine residue,
L is a leucine residue,
W is a tryptophan residue,
T is a threonine residue,
Xaa1 is a lysine residue, a cysteine residue, an aspartic acid residue, a glutamic acid residue, 2-aminosuberic acid, or diaminopropionic acid,
Xaa2 is an alanine residue, a serine residue or a threonine residue,
Xaa3 is a tryptophan residue or a tyrosine residue,
Xaa4 is a histidine residue, an arginine residue, a serine residue or a threonine residue,
Xaa5 is a glutamic acid residue, a glutamine residue, an asparagine residue, an arginine residue, or an aspartic acid residue, and
Xaa6 is an isoleucine residue or a valine residue.

The two cysteine residues in the formula V can form a disulfide bond to form a cyclic peptide. The peptide of the formula V usually has a disulfide bond formed between the two cysteine residues on the outer sides (other than Xaa1, when Xaa 1 is cysteine). Alternatively, in the peptide of the formula V, sulfide groups in the two cysteine residues on the outer sides may be linked via a linker represented by the following formula:

[Formula 4]

In the above formula, the broken line moieties mean binding moieties to the sulfide groups. The linker is more stable against reduction reaction or the like than usual disulfide bonds. Therefore, this linker may be preferably used when using radioactive metal nuclides which may destabilize disulfide bond such as zirconium. This peptide can be prepared by the method described herein.

Several specific examples of the peptide of the formula V are listed below in 18) to 29), though the peptide of the formula V is not limited to them, as a matter of course:

18) DCTYT(Xaa1)GNLVWCT, (SEQ ID NO: 18)

19) DCAYT(Xaa1)GNLVWCT, (SEQ ID NO: 19)

20) DCSYT(Xaa1)GNLVWCT, (SEQ ID NO: 20)

21) DCTWT(Xaa1)GNLVWCT, (SEQ ID NO: 21)

22) DCTYH(Xaa1)GNLVWCT, (SEQ ID NO: 22)

23) DCTYR(Xaa1)GNLVWCT, (SEQ ID NO: 23)

24) DCTYS(Xaa1)GNLVWCT, (SEQ ID NO: 24)

25) DCTYT(Xaa1)GNLVWCT, (SEQ ID NO: 25)

26) DCTYT(Xaa1)GELVWCT, (SEQ ID NO: 26)

27) DCTYT(Xaa1)GRLVWCT, (SEQ ID NO: 27)

28) DCTYT(Xaa1)GDLVWCT, (SEQ ID NO: 28)
and

29) DCTYT(Xaa1)GNLIWCT, (SEQ ID NO: 29)

wherein Xaa1 is a lysine residue, a cysteine residue, an aspartic acid residue, a glutamic acid residue, 2-aminosuberic acid, or diaminopropionic acid.

As mentioned above, the peptide of each formula described above according to the present invention has at least two separate cysteine (C) residues in its amino acid sequence, and the cysteine residues are located to be able to form a disulfide bond between the cysteine residues. Preferably, the peptide is a cyclic peptide having a disulfide bond formed between the two cysteine residues, and may have one or two any amino acid residues other than cysteine at the N terminus and the C terminus of each cysteine residue. When the peptide has one or two amino acid residues at the N terminal side and the C terminal side of each cysteine residue, each of the amino acid residues of 1st, 2nd, 16th, and 17th positions from the N terminus (when the peptide is 17 amino acid residue) is as listed above.

As described above, in the peptide of the present invention, Xaa1 is a protein-constituting amino acid such as a lysine residue, a cysteine residue, an aspartic acid residue, or a glutamic acid residue, or a non-protein-constituting amino acid such as diaminopropionic acid or 2-aminosuberic acid, and is preferably a lysine residue. It is preferred that Xaa1 is modifiable with a cross-linking agent described below. In the present specification, the "non-protein-constituting amino acid" refers to an amino acid that is not used to constitute a protein in an organism. For enhancing site specificity in the modification of the peptide of the present invention with a cross-linking agent, it is preferred that the peptide of the present invention has no or little same residue as Xaa1 (e.g., has only one or two same residues as Xaa1) in its sequence. When Xaa1 is, for example, a lysine residue, it is preferred that the peptide of the present invention has no or little lysine residue at a site other than Xaa1 in its sequence.

The peptide of the present invention has approximately 10 or more times, preferably approximately 50 or more times, more preferably approximately 200 or more times higher binding affinity for human IgG compared with other human immunoglobulins (IgA, IgE, and IgM). A dissociation constant (Kd) as to the binding of the peptide of the present invention to human IgG can be determined by surface plasmon resonance spectroscopy (using, for example, BIA-CORE system) and is, for example, $1\times10^{-1}$ M to less than $1\times10^{-3}$ M, preferably less than $1\times10^{-4}$ M, more preferably less than $1\times10^{-5}$ M.

The IgG-binding peptide of the present invention binds to the Fc domain of IgG. As shown in Examples mentioned later, the IgG-binding peptide of the present invention is placed, at the Xaa1, in proximity to a particular region of IgG Fc, i.e., a Lys248 residue (hereinafter, also simply referred to as "Lys248" in the present specification; which corresponds to the 18th residue of human IgG CH2 (SEQ ID NO: 30)) or a Lys246 residue (hereinafter, also simply referred to as "Lys246" in the present specification; which corresponds to the 16th residue of human IgG CH2 (SEQ ID NO: 30)), preferably Lys248, according to the Eu numbering in human IgG Fc.

The peptide of the present invention can be produced by, for example, a conventional peptide synthesis method such as a liquid-phase synthesis method or a solid-phase synthesis method, or peptide synthesis using an automatic peptide synthesizer (Kelley et al., Genetics Engineering Principles and Methods, Setlow, J. K. eds., Plenum Press NY. (1990) Vol. 12, p. 1-19; S tewart et al., Solid-Phase Peptide Synthesis (1989) W. H. Freeman Co.; Houghten, Proc. Natl. Acad. Sci. USA (1985) 82: p. 5132; and "Shin Seikagaku Jikken Koza (New Biochemical Experimental Lecture Series in English) 1, Protein IV" (1992), ed. by The Japanese Biochemical Society, Tokyo Kagaku Dojin Co., Ltd.). Alternatively, the peptide may be produced by, for example, a gene recombination method using a nucleic acid encoding the peptide of the present invention, or a phage display method. For example, the peptide of interest is produced by incorporating DNA encoding the amino acid sequence of the peptide of the present invention into an expression vector, transferring it to host cells, and then culturing them. The produced peptide can be collected or purified by a routine method, for example, chromatography such as gel filtration chromatography, ion-exchange column chromatography, affinity chromatography, reverse-phase column chromatography, or HPLC, ammonium sulfate fractionation, ultrafiltration, and/or immunoadsorption.

In the peptide synthesis, for example, amino acids are prepared such that the functional groups, except for an α-amino group and an α-carboxyl group for use in bonds, of these amino acids (regardless of being natural or non-natural) are protected. Peptide bond formation reaction is performed between the α-amino group of one amino acid and the α-carboxyl group of another. Usually, the carboxyl group of an amino acid residue positioned at the C terminus of the peptide is immobilized onto a solid phase via an appropriate spacer or linker. The protective group at the amino terminus of the dipeptide thus obtained is selectively removed, and a peptide bond is formed between the deprotected amino group and the α-carboxyl group of the subsequent amino acid. A peptide having protected side groups is produced by continuously performing such operation. Finally, all of the protective groups are removed, and the peptide is separated from the solid phase. Details about the type of the protective group, the protection method, and the peptide bond method are described in the literatures described above.

The production by the gene recombination method can be performed by a method which involves, for example, inserting DNA encoding the peptide of the present invention into an appropriate expression vector, transferring the vector to appropriate host cells, culturing the cells, and collecting the peptide of interest from the inside of the cells or the extracellular fluid. The vector is not limited and is, for example, a vector such as a plasmid, a phage, a cosmid, a phagemid, or a virus. Examples of the plasmid vector include, but are not limited to, *E. coli*-derived plasmids (such as pET22b(+), pBR322, pBR325, pUC118, pUC119, pUC18, pUC19, and pBluescript), *Bacillus subtilis*-derived plasmids (such as pUB110 and pTP5), and yeast-derived plasmids (such as YEp13 and YCp50). Examples of the phage vector include, but are not limited to, T7 phage display vectors (such as T7Select 10-3b, T7Select 1-1b, T7Select 1-2a, T7Select 1-2b, T7Select 1-2c (Novagen)), and λ phage vectors (such as Charon 4A, Charon 21A, EMBL3, EMBL4, λgt10, λgt11, λZAP, λZAPII). Examples of the virus vector include, but are not limited to, animal viruses such as retrovirus, adenovirus, adeno-associated virus, vaccinia virus, and hemagglutinating virus of Japan, and insect viruses such as baculovirus. Examples of the cosmid vector include, but are not limited to, Lorist 6, Charomid 9-20, and Charomid 9-42. The phagemid vector is not limited, and, for example, pSKAN, pBluescript, pBK, and pComb3H are known. The vector may contain a control sequence that permits expression of the DNA of interest, a selective marker for the selection of a vector containing the DNA of interest, a multicloning site for insertion of the DNA of interest, and the like. Such a control sequence includes, for example, a promoter, an enhancer, a terminator, a S-D sequence or a ribosomal binding site, a replication origin, and a poly-A site. For example, an ampicillin resistance gene, a neomycin resistance gene, a kanamycin resistance gene, or a dihydrofolate reductase gene can be used as the selective marker. The host cells to which the vector is transferred are, for example, cells of a bacterium such as *E. coli* or *Bacillus subtilis*, yeast cells, insect cells, animal cells (such as mammalian cells), or plant cells. The transformation or transfection of these cells includes, for example, a calcium phosphate method, electroporation, a lipofection method, a particle gun method, and a PEG method. The culture of the transformed cells is performed according to an ordinary method for use in the culture of host organisms. For example, a culture solution for a microbe such as *E. coli* or yeast cells contains a carbon source, a nitrogen source, and inorganic salts, etc. utilizable by the host microbe. For facilitating collecting the peptide of the present invention, it is preferred that the peptide produced by expression should be secreted into the outside of the cells. This can be performed by linking DNA encoding a peptide sequence that permits secretion of the peptide from the cells, to the 5' end of DNA encoding the peptide of interest. The fusion peptide transferred to the cell membrane is cleaved by signal peptidase so that the peptide of interest is secreted and released into the medium. Alternatively, the peptide of interest accumulated in the cells may be collected. In this case, the cells are disrupted physically or chemically, and the peptide of interest is collected by use of a protein purification technique.

Hence, the present invention further relates to a nucleic acid encoding the peptide of the present invention. In this context, the nucleic acid includes DNA or RNA (such as mRNA).

When the IgG-binding peptide of the present invention is fused with another protein, the IgG-binding peptide and another protein may be separately prepared and then fused using a linker, if necessary, or may be prepared as a fusion protein with an optionally added appropriate linker by a gene recombination method. In this case, the fusion protein is preferably prepared so as not to impair the binding activity of the IgG-binding peptide of the present invention against IgG.

<Peptide Modified with Cross-Linking Agent>

In one aspect, the IgG-binding peptide according to the present invention is preferably modified with a cross-linking agent.

As described above, the IgG-binding peptide of the present invention is placed, at the Xaa1, in proximity to a particular region of IgG Fc, i.e., Lys248 or Lys246, preferably Lys248, according to the Eu numbering in human IgG Fc, as shown in Examples mentioned later. Thus, a cross-linked structure can be site-specifically formed between the Xaa1 of the IgG-binding peptide and Lys248 or Lys246, preferably Lys248, of IgG Fc, by modifying Xaa1 of the IgG-binding peptide of the present invention with a cross-linking agent, followed by cross-linking reaction of the peptide with IgG. Various compounds can be introduced specifically and conveniently to IgG by modifying Xaa1 of the IgG-binding peptide of the present invention with a cross-linking agent and the various compounds, followed by cross-linking reaction of the peptide with the IgG, as described above. According to the present invention, compounds can be introduced via the IgG-binding peptide. Therefore, compounds having various structures can be introduced to IgG. Furthermore, the method of the present invention has high yields of products to be obtained and does not involve the engineering of antibodies themselves. Therefore, the method of the present invention also has the advantage that the method is unlikely to reduce the functions of the antibodies.

The IgG-binding peptide of the present invention can also be used for IgG of a non-human animal, preferably a mammal. In this case, those skilled in the art who have read the present specification can easily identify a site in IgG to which the IgG-binding peptide of the present invention binds, for example, by aligning the sequence of human IgG with the sequence of IgG of a different animal.

In the present invention, the "cross-linking agent" is a chemical substance for linking the IgG-binding peptide of the present invention to IgG Fc via a covalent bond. The cross-linking agent of the present invention can be appropriately selected by those skilled in the art and can be a compound having at least two sites capable of binding to the desired amino acids (such as a lysine residue, a cysteine residue, an aspartic acid residue, a glutamic acid residue, 2-aminosuberic acid, or diaminopropionic acid, and arginine). Examples thereof include, but are not limited to: cross-linking agents containing preferably two or more succinimidyl groups, such as DSG (disuccinimidyl glutarate) and DSS (disuccinimidyl suberate); cross-linking agents containing preferably two or more imidic acid moieties, such as DMA (dimethyl adipimidate dihydrochloride), DMP (dimethyl pimelimidate dihydrochloride), and DMS (dimethyl suberimidate dihydrochloride); and cross-linking agents having a SS bond, such as DTBP (dimethyl 3,3'-dithiobispropionimidate dihydrochloride) and DSP (dithiobis(succinimidyl propionate)).

The IgG-binding peptide of the present invention may be modified with an additional functional substance, for example, an antibody such as IgA or VHH, a labeling agent and/or an additional drug. The linking of the IgG-binding peptide to the additional functional substance can be performed by a method known to those skilled in the art, for example, the reaction between an azide group and dibenzocyclooctyne or the reaction between a maleimide group and a sulfhydryl group. The IgG can be detected or quantified via the labeling agent, when the IgG-binding peptide of the present invention labeled with a labeling agent forms a conjugate with IgG. Examples of the labeling agent include, but are not limited to, the radioactive metal nuclides described above, fluorescent dyes, chemiluminescent dyes, biotin, fluorescent proteins such as GFP (green fluorescent protein), luminescent proteins, and enzymes such as peroxidase. As a preferred example, the labeling agent is a fluorescent dye including fluorescein and fluorescein derivatives such as FITC, rhodamine and rhodamine derivatives such as tetramethylrhodamine, and Texas Red. In the case of modifying the peptide of the present invention with an additional drug, examples of the drug include, but are not limited to: anticancer agents such as auristatin, maytansine, emtansine, doxorubicin, bleomycin, and their derivatives; and targeting agents such as drugs that permit transfer to the central nerve through binding to a receptor on the blood-brain barrier, and drugs that permit transfer of an antibody into cancer cells or the like through binding to the cells.

The IgG-binding peptide modified with a cross-linking agent according to the present invention can be produced, for example, by reacting the IgG-binding peptide obtained according to the method described in the above section <IgG-binding peptide> with the cross-linking agent. In this case, the side chain of the amino acid residue Xaa1 in the IgG-binding peptide needs to be specifically modified. This can be achieved by selecting, for example, the type of the Xaa1 and its combination with the cross-linking agent. For example, the cross-linking agent containing succinimidyl groups, such as DSS or DSG, reacts with primary amines present at the side chain of a lysine residue and the N terminus of a polypeptide. Therefore, the N terminus of the IgG-binding peptide is blocked, and then, the IgG-binding peptide can be reacted with DSS or DSG to specifically modify only the side chain of the lysine residue with the DSS or the DSG. Such a combination of the amino acid residue with the cross-linking agent can be appropriately selected by those skilled in the art.

The IgG-binding peptide modified with a cross-linking agent according to the present invention can also be produced by peptide synthesis using, for example, an amino acid residue modified with the cross-linking agent. Likewise, in the case of modifying the IgG-binding peptide with a labeling agent and/or an additional drug, the IgG-binding peptide modified with the labeling agent and/or the additional drug may be prepared by peptide synthesis using an amino acid residue thus modified.

Also, the IgG-binding peptide of the present invention may be modified by, for example, N-terminal PEGylation (polyethylene glycol addition) and/or C-terminal amidation, to improve the stability of the IgG-binding peptide, etc. For the PEGylation, the number of PEG molecules is not particularly limited. For example, 1 to 50 molecules, 1 to 20 molecules, 2 to 10 molecules, 2 to 6 molecules, or 4 molecules of PEG can be added thereto.

<Cross-Linking Reaction>

In one aspect, the present invention relates to a method for producing a conjugate of an IgG-binding peptide and IgG, comprising the step of mixing the IgG-binding peptide modified with a cross-linking agent according to the present invention with the IgG. This step can cause cross-linking reaction between the IgG-binding peptide modified with a cross-linking agent and the IgG. The cross-linking reaction can occur site-specifically, particularly, between the amino acid residue Xaa1 of the IgG-binding peptide and Lys248 or Lys246, preferably Lys248, of IgG Fc.

Conditions for the mixing step are not particularly limited as long as the conditions result in the cross-linking reaction between the IgG-binding peptide of the present invention and the IgG. For example, the IgG-binding peptide of the present invention and the IgG can be reacted by mixing at room temperature (such as approximately 15° C. to 30° C.) in an appropriate buffer. The mixing step may be performed by the addition of a catalyst that accelerates the cross-linking reaction in an appropriate amount, if necessary.

The mixing ratio between the IgG-binding peptide of the present invention and the IgG in the mixing step is not particularly limited. The molar ratio between the IgG-binding peptide of the present invention and the IgG can be set to, for example, 1:1 to 20:1, preferably 2:1 to 20:1 or 5:1 to 10:1.

The mixing time (reaction time) in the mixing step is not limited as long as the mixing time results in the cross-linking reaction between the IgG-binding peptide of the present invention and the IgG. The mixing time can be, for example, 1 minute to 5 hours, preferably 10 minutes to 2 hours or 15 minutes to 1 hour.

The method for producing a conjugate of the IgG-binding peptide of the present invention and IgG may further comprise, if necessary, the step of purifying the conjugate by separating impurities, for example, unreacted IgG-binding peptides and IgG, and reagents, from the mixture after the step described above. This step can be performed by a method known in the art, for example, chromatography such as gel filtration chromatography, ion-exchange column chromatography, affinity chromatography, reverse-phase column chromatography, or HPLC.

<Conjugate>

In one aspect, the present invention relates to a conjugate of the IgG-binding peptide of the present invention and IgG. The conjugate can be formed through the cross-linking reaction described above. Accordingly, the present invention preferably relates to a conjugate of the IgG-binding peptide and IgG, wherein the amino acid residue Xaa1 of the IgG-binding peptide is site-specifically linked to Lys248 or Lys246, preferably Lys248, of IgG Fc via a cross-linking agent.

Since the conjugate of the present invention is formed through site-specific cross-linking reaction, the cross-linking reaction is unlikely to negatively influence the activity of metal nuclide such as $^{111}$In, $^{89}$Zr, $^{64}$Cu, $^{67/68}$Ga, or $^{99m}$Tc added thereto can be used for the detection or diagnosis of cancer. In this case, the IgG can be appropriately selected depending on the type of the cancer. For example, trastuzumab can be used for breast cancer, and cetuximab can be used for colorectal cancer.

<Radionuclide Imaging Agent or Diagnostic Agent for Cancer, and Radionuclide Imaging Method or Method for Determining Presence or Absence of Cancer>

In one aspect, the present invention relates to a radionuclide imaging agent or a diagnostic agent for cancer comprising the IgG-binding peptide bound with a radioactive metal nuclide, the IgG-binding peptide modified with a cross-linking agent, or the conjugate of the IgG-binding peptide modified with a cross-linking agent and IgG.

The radionuclide imaging agent of the present invention can be used for measuring the distributions and/or pharmacokinetics of various substances in vivo. For example, the radionuclide imaging agent comprising the conjugate of the IgG-binding peptide of the present invention and IgG can be used for measuring the distributions of antigens such as inflammatory markers targeted by IgG, and the pharmacokinetics of the IgG antibody itself.

Examples of the cancer targeted by the diagnostic agent for cancer of the present invention include, but are not limited to, breast cancer, liver cancer, pancreatic cancer, prostate cancer, ovary cancer, colorectal cancer (e.g., colon cancer), stomach cancer, uterine cervical cancer, brain tumor, myeloma, osteosarcoma, lung cancer, leukemia and malignant lymphoma.

The radionuclide imaging agent or the diagnostic agent for cancer of the present invention can be administered by oral administration or parenteral administration (such as intravenous injection, intramuscular injection, subcutaneous administration, intraperitoneal administration, rectal administration, or transmucosal administration). The radionuclide imaging agent or the diagnostic agent for cancer of the present invention can be in an appropriate dosage form depending on the administration route. Specifically, the radionuclide imaging agent or the diagnostic agent for cancer of the present invention can be prepared as various forms of preparations including granules, tablets, pills, capsules, syrups, emulsions, suspensions, injections for intravenous injection, intraarterial injection, or intramuscular injection, drops, agents for external use, and suppositories. The administration method and the dosage form can be appropriately selected by those skilled in the art depending on the sex, age, body weight, symptoms, etc. of a patient.

The radionuclide imaging agent or the diagnostic agent for cancer of the present invention can be formulated according to a routine method (see, for example, Remington's Pharmaceutical Science, latest edition, Mark Publishing Company, Easton, USA) and may also contain a pharmaceutically acceptable carrier or additive.

Examples of the carrier and the pharmaceutical additive that may be contained in the radionuclide imaging agent or the diagnostic agent for cancer of the present invention include water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerin, glycerin, propylene glycol, Vaseline, paraffin, stearyl alcohol, stearic acid, human serum albumin (HSA), mannitol, sorbitol, lactose, and surfactants acceptable as pharmaceutical additives.

Actual additives are selected alone or in appropriate combination from among those described above according to the dosage form of the radionuclide imaging agent or the diagnostic agent for cancer of the present invention, though the additives are not limited to them. For example, for use as a preparation for injection, the IgG-binding protein of the present invention or the conjugate of the IgG-binding protein and IgG is dissolved in a solution, for example, saline, a buffer solution, or a glucose solution, to which an agent preventing adsorption onto containers, for example, Tween 80, Tween 20, gelatin, or human serum albumin, is added. The resulting mixture can be used. Alternatively, a freeze-dried product may be used for a dosage form that is reconstituted by thawing before use. For example, a sugar alcohol and/or a saccharide, such as mannitol or glucose, can be used as a stabilizer for the freeze drying.

The effective dose and dosing interval of the radionuclide imaging agent or the diagnostic agent for cancer of the present invention can be appropriately selected depending on the sex, age, body weight, and symptoms, etc. of a patient.

In one aspect, the present invention relates to a method for determining the presence or absence of cancer in a subject, comprising the steps of:
  reacting a sample obtained from the subject with the IgG-binding peptide or the conjugate of the IgG-binding peptide and IgG described in the present specification, wherein a radioactive metal nuclide is bound to the IgG-binding peptide;
  measuring a level or presence of radioactivity derived from the radioactive metal nuclide in the sample; and
  determining the presence or absence of cancer in the subject on the basis of the level or presence of radioactivity.

In one aspect, the present invention relates to a method for detecting an antigen or IgG in a subject, comprising the steps of:
  reacting a sample obtained from the subject with the conjugate of the IgG-binding peptide and IgG described in the present specification, wherein a radioactive metal nuclide is bound to the IgG-binding peptide;
  measuring a level or presence of radioactivity derived from the radioactive metal nuclide in the sample; and
  detecting the antigen or IgG on the basis of the level or presence of radioactivity. The distribution and/or pharmacokinetics of the antigen or IgG in the subject can be predicted by detecting the antigen or IgG in the sample.
Examples of the sample for use in this method include tissues and biological samples. Examples of the tissues include tissues of lesion sites, for example, the breast, the liver, the pancreas, the prostate, the ovary, the large intestine (e.g., the colon), the stomach, the uterine cervix, bone marrow, and lymph nodes. For example, biopsy samples of these tissues can be used. Examples of the biological samples include blood, plasma, lymph, tissue fluid, urine, and cells, for example, peripheral blood cells, trichogen cells, buccal cells, nasal cells, intestinal cells, vaginal cells, mucosal cells, and expectoration (which may include alveolar cells and tracheal cells, etc.), preferably blood and plasma.

The method for measuring the level or presence of radioactivity is not particularly limited, and any method known to those skilled in the art can be used. For example, image analysis such as SPECT/CT may be conducted, or the level or presence of radioactivity may be measured using a detector such as a scintillation counter.

The step of determining or detecting the presence or absence of cancer in the subject on the basis of the level or presence of radioactivity is not particularly limited, and any method known to those skilled in the art can be used. For example, it can be determined that the subject is likely to have cancer when the level of radioactivity in the sample derived from the subject subjected to the method of the present invention is significantly higher than that of a plurality of, for example, 2 or more, 3 or more, or 4 or more, preferably 5 or more samples derived from subjects confirmed to have no cancer.

In one aspect, the present invention relates to a method for determining the presence or absence of cancer in a subject, comprising the steps of:
  administering the IgG-binding peptide or the conjugate of the IgG-binding peptide and IgG described in the present specification to the subject, wherein a radioactive metal nuclide is bound to the IgG-binding peptide;
  measuring a level or presence of radioactivity derived from the radioactive metal nuclide in the subject; and
  determining the presence or absence of cancer in the subject on the basis of the level or presence of radioactivity.

In one aspect, the present invention relates to a method for detecting an antigen or IgG in a subject, comprising the steps of:
  administering the conjugate of the IgG-binding peptide and IgG described in the present specification to the subject, wherein a radioactive metal nuclide is bound to the IgG-binding peptide;
  measuring a level or presence of radioactivity derived from the radioactive metal nuclide in the subject; and
  detecting the antigen or IgG on the basis of the level or presence of radioactivity. This method is preferably a radionuclide imaging method. The distribution and/or pharmacokinetics of the antigen or IgG in the subject can be predicted by this method.

In this method, the administration method is the same as that described about the radionuclide imaging agent or the diagnostic agent for cancer of the present invention, so that the description is omitted. Also, the step of measuring a level or presence of radioactivity and the step of determining the presence or absence of cancer in the subject are as described above, so that the description is omitted.

In the present specification, examples of the organism species of the subject include: primates such as humans and chimpanzees; laboratory animals such as rats, mice, and rabbits; livestock animals such as pigs, cattle, horses, sheep, and goats; and pet animals such as dogs and cats. A human is preferred.

EXAMPLES

Although the present invention will be described in further detail with reference to Examples below, the scope of the present invention shall not be limited by these Examples.

Example 1: X-Ray Crystallography of Conjugate of IgG-Binding Peptide and IgG <Method>
(1) Preparation of IgG-Binding Peptide Solution A cyclic homocysteine peptide having the sequence of G(HC)DCAYHRGELVWCT(HC)H—NH$_2$ (SEQ ID NO: 31, wherein HC represents homocysteine, and the two Cys residues at positions 4 and 14 and the two homocysteine residues at positions 2 and 16 respectively formed intramolecular disulfide bonds) was prepared according to a routine method by the solid-phase peptide synthesis method based on the Fmoc method. A powder of 0.8 mg of the prepared IgG-binding peptide was dissolved in 24 μL of 100% dimethyl sulfoxide (Wako Pure Chemical Industries, Ltd.) to prepare an IgG-binding peptide solution.

(2) Preparation of Conjugate of Fc and IgG-Binding Peptide

The hinge moiety of human IgG (Chugai Pharmaceutical Co., Ltd.) was cleaved using papain (manufactured by F. Hoffmann-La Roche, Ltd.) at 37° C. in a 20 μmol/L phosphate buffer solution (pH 7.0) containing 10 mM EDTA and 1 mM L-cysteine. Subsequently, human IgG Fc was purified by gradient elution of 0 to 0.3 M NaCl in a 20 mM sodium acetate buffer solution (pH 5.0) at a flow rate of 1 mL/min using a cation-exchange column (TSKgel SP5-PW (Tosoh Corp.)). 63 μL of a solution (0.1 M sodium chloride (Wako Pure Chemical Industries, Ltd.) and 0.04 M 2-morpholinoethanesulfonic acid (Wako Pure Chemical Industries, Ltd.) (pH 6.0)) containing 16 mg/mL human IgG Fc was mixed with 2 μL of the IgG-binding peptide solution prepared in the preceding section (1) to prepare a Fc/IgG-binding peptide conjugate solution.

(3) Preparation of Crystal of Fc/IgG-Binding Peptide Conjugate

Crystals of the Fc/IgG-binding peptide conjugate were obtained by the sitting drop vapor diffusion method. Specifically, 0.3 μL of the Fc/IgG-binding peptide conjugate solution prepared in the preceding section (2) and 0.3 μL of a crystallizing agent (20% polyethylene glycol 3350 (Sigma-Aldrich Co. LLC) and 0.2 M potassium iodide (Wako Pure Chemical Industries, Ltd.) (pH 6.9)) were mixed on 51 wells of Intelli-Plate for Crystallization (manufactured by VERITAS Corp.) using Hydra II+ (manufactured by Matrix Technologies Corp.), which is a robot for crystallization, to prepare crystallized drops. 70 μL of the crystallizing agent was dispensed thereto as a reservoir solution. The plate was hermetically sealed using PowerSeal CRISTAL VIEW (manufactured by Greiner Bio-One Co., Ltd.) and then left standing for approximately 2 weeks in a thermostat bath of 20° C. to obtain crystals.

(4) Collection of X-Ray Diffraction Intensity Data on Crystal of Fc/IgG-Binding Peptide Conjugate The crystals obtained in the preceding section (3) were transferred to a stabilizing mother liquor (22% polyethylene glycol 3350, 0.2 M potassium iodide, 0.1 M sodium chloride, 25% glycerol (w/v), and 0.04 M 2-morpholinoethanesulfonic acid (pH 6.0)) and rapidly frozen under stream of nitrogen gas of −170° C., and X-ray diffraction data was determined by the oscillation method. The assay was carried out at an X-ray wavelength of 1 angstrom and an angle of oscillation of 1°/frame. Next, the diffraction intensity data was processed at a resolution of 3.0 angstroms using a diffraction intensity data processing program HKL2000 (manufactured by HKL Research Inc.). As a result, the space group of the crystals was P21, and the lattice constants were a=66.1 angstroms, b=60.5 angstroms, c=69.5 angstroms, α=γ=90°, and β=101.3°. The obtained data had 99.9% completeness and 13.8% Rmerge.

(5) Determination of Crystal Structure of Fc/IgG-Binding Peptide Conjugate

The phase determination of DCAYHRGELVWCT (SEQ ID NO: 33) by the molecular replacement method was attempted using the diffraction intensity data obtained in the preceding section (4) and a program Phaser included in CCP4 (Collaborative Computational Project Number 4). A Fc moiety model registered as PDB accession code: 1DN2 in the Protein Data Bank (PDB) was utilized as a search model for the molecular replacement method. As a result, a model of one molecule in an asymmetric unit was able to be found. Next, structure refinement using a structure refinement program Refmac5 included in CCP4 and model correction using a model construction program X-tal view were repetitively carried out to obtain the crystal structure of the conjugate of the Fc and the IgG-binding peptide (DCAYHRGELVWCT (SEQ ID NO: 33)). The density of electrons corresponding to the IgG-binding peptide was observed in the peptide-binding site of the Fc. The R factor serving as an index for the accuracy of the determined crystal structure was 0.216. The Rfree factor calculated from structural factors corresponding to 5% of the total reflection, which was excluded from calculation at the stage of refinement, was 0.317.

(6) Preparation of Cross-Linked Structure Model

On the basis of the structure in the X-ray crystallography, a cross-linked structure model was prepared on computational science software MOE (Molecular Operating Environment). After substitution of the 6th amino acid of DCAYHRGELVWCT (SEQ ID NO: 33) by Lys, a cross-linked structure via DSG or DSS was converted to a model in a form having a linkage between the c amino group of this Lys and the c amino group of Lys at position 248 of the antibody Fc.

<Results>

As shown in FIG. 1A, the IgG-binding peptide seemed to bind to the boundary region between CH2 and CH3 domains overlapping with a binding site for protein A, and bind to IgG in a manner similar to a previously reported IgG-binding peptide Fc-III (DeLano, W. L. et al., Science, 2000, 287, pp. 1279-1283). The characteristic interaction between the IgG-binding peptide and Fc is the salt linkage of the guanidino group of the side chain of the 8th residue Arg in the IgG-binding peptide to the carboxylic acid of the side chain of Glu380 (based on the EU numbering; the same also applies hereinbelow) in the Fc at 2.91 angstroms. The side chain of this Glu380 forms an intramolecular salt linkage network through the salt linkage to Lys248 in human IgG Fc. Arg8 of the IgG-binding peptide and Lys248 of Fc were positioned close to each other via the interaction with Glu380 of the Fc. Accordingly, the 8th residue Arg of the IgG-binding peptide was changed to Lys, and the cross-linkage between Lys8 of the peptide and the side chain amino group of Lys248 of the antibody via a cross-linking agent was discussed in a form similar to this salt linkage network structure. A model of a cross-linked structure via DSG (disuccinimidyl glutarate) or DSS (disuccinimidyl suberate) was actually prepared on the basis of the conjugate structure of the IgG-binding peptide and human IgG Fc. As a result, the introduction of the cross-linking agent seemed to be possible without causing the spatial distortion of the main chain structure of the antibody (FIG. 1B).

Example 2: Preparation and Properties of Peptide for Labeling

<Method>

An amino-PEG4-added synthetic peptide GPD-CAYHXGELVWCTFH (SEQ ID NO: 2) (C-terminally amidated) with the amino group modified with biotin or 5/6 TAMURA succinimidyl ester (AnaSpec, Inc.) (fluorescent dye) was synthesized according to a routine method by the Fmoc solid-phase synthesis method. After removal of protective groups, an intramolecular S—S bond was formed under oxidative conditions in an aqueous solution of pH 8.5. The peptide having the intramolecular S—S bond was purified using reverse-phase HPLC by gradient elution of 10% to 60% acetonitrile containing 0.1% TFA at a flow rate of 1.0 ml/min.

100 μL of a DMF solution containing 1 mM of the purified IgG-binding peptide was mixed with 100 μL of an acetonitrile solution of 100 mM DSS or DSG (Thermo Fisher Scientific Inc.), and the mixture was then reacted overnight at room temperature. The reaction product was diluted 2.5-fold with 0.1% TFA and then injected to μ Bondasphere 5 C18 100 angstroms (3.9 mm in diameter×150 mm) manufactured by Waters Corp., followed by elution in a gradient of 4% to 60% acetonitrile containing 0.1% TFA. The addition of the cross-linking agent to the obtained product was confirmed by elution in a gradient of 4% to 60% acetonitrile containing 0.1% formic acid on LC-Mass spectrometry (Acquity SQD UPLC system, Waters Corp.) connected with BEH300 C18 (1.7 μm, 2.1 mm in diameter×50 mm) column, and the subsequent measurement of the molecular weights of peaks.

The affinity analysis of the obtained labeled reagent peptide was conducted by a method described below after addition of 1 M Tris-HCl (pH=7.0) in an amount of 1/10 and hydrolysis of the NHS group through reaction for 15 minutes. 0.4 M EDC (1-ethyl-3-(3-dimethylaminopropyl)-carbodiimide) and 0.1 M sulfo-NHS (sulfo-N-hydroxysuccinimide) were mixed in equal amounts and then injected onto a CMS sensor chip loaded in BIAcore T200 (GE Healthcare Japan Corp.) for 7 minutes at a flow rate of 10 μl/ml to activate the sensor chip. IgG was immobilized thereonto in an amount of 4000 to 5000 in terms of RU value under conditions of pH 4.0 (10 mM sodium acetate). While a HBS-EP buffer solution (0.01 M HEPES, 0.15 M NaCl, 0.005% Tween 20, and 3 mM EDTA, pH 7.0) was used, binding reaction was monitored by the injection of the peptide at a concentration of 10 nM to 2 μM for 180 seconds at a flow rate of 50 μl/ml. Then, dissociation reaction was assayed by washing with a buffer solution for 600 seconds. Binding parameters were analyzed using BIAevalution T100 software.

<Results>

In order to study whether the introduction of the cross-linked structure would influence the specificity and affinity of the IgG-binding peptide, the binding activity of the IgG-binding peptide having the introduced cross-linked structure against IgG was measured by SPR analysis (Table 1). The affinity of the IgG-binding peptide in which the 8th residue arginine was substituted by lysine (hereinafter, also referred to Type I(R8K)) for human IgG was 131 nM (Kd), which was decreased by 10 times as compared with the affinity of the IgG-binding peptide before the substitution (hereinafter, also referred to as Type I). The affinity of the Type I(R8K) peptide bound to each cross-linking agent for human IgG was approximately 330 nM (Kd) (Type I(R8K)-DSG-OH) and approximately 390 nM (Kd) (Type I(R8K)-DSS-OH), showing no large decrease in affinity due to the binding of the cross-linking agent. All of the peptides had affinity of 04 or lower in terms of Kd value, suggesting sufficiently specific labeling is achieved.

TABLE 1

(SEQ ID NOS 45-48, respectively, in order of appearance)

| Peptide | Sequence | ka | kd | 1:1 binding | KD (nM) Equilibrium value |
|---|---|---|---|---|---|
| Type I | GPDCAYHRGELVWCTFH-NH$_2$ | 1.57E+06 | 0.0144 | 9.1 | 10 |
| Type I(R8K) | GDDCAYHKGELVWCTFH-NH$_2$ | 1.25E+06 | 0.195 | 156 | 131 |
| Type I(R8K)-DSG-OH | GDDCAYHK(DSG-OH)GELVWCTFH-NH$_2$ | 3.29E+05 | 0.1036 | 315 | 330 |
| Type I(R8K)-DSS-OH | GDDCAYHK(DSS-OH)GELVWCTFH-NH$_2$ | 1.68E+05 | 0.06136 | 365 | 389 |

Affinity of hydrolysates of Type I(R8K) and each cross-linking agent-bound peptide (all of the peptides used were N-terminally blocked with biotinylated PEG4). Type I(R8K)-DSG-OH and Type I(R8K)-DSS-OH represent products obtained by the hydrolysis of the NHS group of the introduced cross-linking agent in Type I(R8K).

Example 3: Specific Modification of Human IgG-Fc with IgG-Binding Peptide

<Method>

A labeled reagent peptide was prepared in the same way as in Example 2 by modifying a N-terminally biotin-PEG4-added IgG-binding peptide (Type I(R8K)) with DSS or DSG. This peptide was reacted with human IgG Fc to study the labeling reaction of the human IgG Fc. Specifically, an IgG-binding peptide (R8K) (200 pmol/5 μL in 0.1% TFA) reacted with an excess of DSS or DSG in the same way as in Example 2 was purified with a reverse-phase column, followed by the removal of acetonitrile under reduced pressure. Then, the purified product was neutralized by the addition of 0.5 M Na$_2$HPO$_4$ in an amount of approximately 1/8 and immediately added at a molar ratio of 10 times to a protein sample (hIgG (Chugai Pharmaceutical Co., Ltd.), hIgA (Athens Research & Technology, Inc.), HAS (Sigma-Aldrich Co. LLC), or serum (collected from a healthy person)) (40 pmol/5 μL for each sample; the serum used was diluted 10-fold with PBS). After adjustment of the final amount to 20 μL with PBS, the mixture was left at room temperature for 5 minutes. Then, the reaction was terminated by the addition of 1 μl of 1 M Tris-HCl (pH=7.0).

Then, 6.7 μl of 4×SDS sample solution and 1.4 μl of 2-mercaptoethanol (final concentration: 5%) were added thereto, and the mixture was treated at 95° C. for 10 minutes, followed by SDS-PAGE using a precast gel SuperSep™ Ace, 5-20% (Wako Pure Chemical Industries, Ltd.). The gel after the electrophoresis was transferred to a PMDF membrane at 35 mA for 60 minutes using Hoefer Semiphor TE70 transblot system. Then, the membrane was blocked with 0.5% BSA. The protein labeled with the biotinylated peptide was detected using SA-conjugated HRP (diluted 1000-fold, Vector Laboratories, Inc.) and a chemiluminescent reagent (ImmunoStar® Basic, Wako Pure Chemical Industries, Ltd.).
<Results>

As shown in FIG. 2B, a band considered to be derived from the conjugate was observed only in the reaction with IgG in Western blotting, demonstrating that both of the IgG-binding peptides reacted with DSG or DSS selectively bind to IgG without binding to IgA, HAS, and proteins other than IgG in serum.

Example 4: Study on Conditions for Reaction of IgG-Binding Peptide with IgG

<Method>
(1) Study on Reaction Molar Ratio

A 0.1 M NaHCO$_3$ solution containing each protein (IgG (Chugai Pharmaceutical Co., Ltd.), IgA (Athens Research & Technology, Inc.), or bovine gelatin (Wako Pure Chemical Industries, Ltd.)) (50 ng (0.33 pmol)/μl/well) was added to wells of a 96-well microplate (Nunc® MaxiSorp), and the plate was left overnight at room temperature to adsorb each protein onto the surface of the plate. After blocking with 0.5% BSA, a biotinylated IgG-binding peptide modified with DSG (molar ratio: 0, 1, 2, 5, or 10), prepared in the same way as in Example 2 was added to each well. After 1 hour, the reaction was terminated by the addition of 1 M Tris-HCl (pH 7.0) at 3 μL/well. SA-HRP (Vector Laboratories, Inc.) diluted 2000-fold with 0.5% BSA was added thereto at 50 μL/well and reacted at room temperature for 1 hour. Then, the plate was washed five times with 0.1% PBST. Then, a TMB solution (Wako Pure Chemical Industries, Ltd.) was used in the color development of HRP. After 5-minute chromogenic reaction, the absorbance at 450 nm was measured using an ELISA plate reader (model 680 microplate reader (Bio-Rad Laboratories, Inc.)).
(2) Study on Reaction Time The biotinylated IgG-binding peptide modified with DSG was added at a molar ratio of 2 to hIgG (50 ng) immobilized overnight at 4° C. with a 50 ng/50 μL solution. After each reaction time (0 to 60 minutes), the reaction was terminated by the addition of 3 μL of 1 M Tris-HCl (pH 7.0). The binding was detected in the same way as in (A).
<Results>

Reaction efficiency based on different numbers of moles for reaction with the antibody and reaction times was studied by ELISA using the labeled IgG-binding peptide modified with DSS (FIG. 3). Specifically, the IgG-binding peptide immobilized on a plastic plate was reacted at varying molar ratios from 1 to 10 with hIgG. As a result, saturation was seen at a molar ratio of almost 5, suggesting that the addition of the peptide reagent at a molar ratio of approximately 5 suffices for antibody labeling (FIG. 3A). Very weak binding was seen in a biotinylated IgG-binding (R8K) peptide unmodified with DSS (NO DSS R8K). This may be derived from the binding activity of a peptide bound via a noncovalent bond. Even though an excess of the labeled IgG-binding peptide reagent was added, the binding to other proteins (hIgA, bovine gelatin, or BSA used as a blocking agent) was not detected.

Next, the reaction time was studied when IgG and the IgG-binding peptide were reacted at a molar ratio of 1:2. As a result, saturation was seen after approximately 15 minutes, suggesting that the reaction almost completed in 15 minutes (FIG. 3B).

These results indicated that the IgG-binding peptide of the present invention modified with a cross-linking agent specifically binds to IgG in a short time.

Example 5: Labeling of Fc with Fluorescent IgG-Binding Peptide

<Method>

IgG (Chugai Pharmaceutical Co., Ltd.), IgA (Athens Research & Technology, Inc.), or BSA (Sigma-Aldrich Co. LLC) (15 μg: 100 pmol in terms of IgG) and a DSG-crosslinked peptide or a DSS-crosslinked peptide (500 pmol) prepared according to Example 2 were reacted at room temperature for 60 minutes in 200 μL. The reaction was terminated by the addition of 10 μL of 1 M Tris-HCl (pH=7.0). Then, size exclusion chromatography was performed using Superdex™ 200 10/30GL 1.0 cm in diameter× 30 cm (GE Healthcare Japan Corp.); flow rate: 0.3 ml/min; running buffer: PBS pH 7.4. Assay was conducted using a fluorescence detector RF-10A (Shimadzu Corp.) (excitation light: 541 nm, fluorescence: 565 nm).
<Results>

Figure 4:
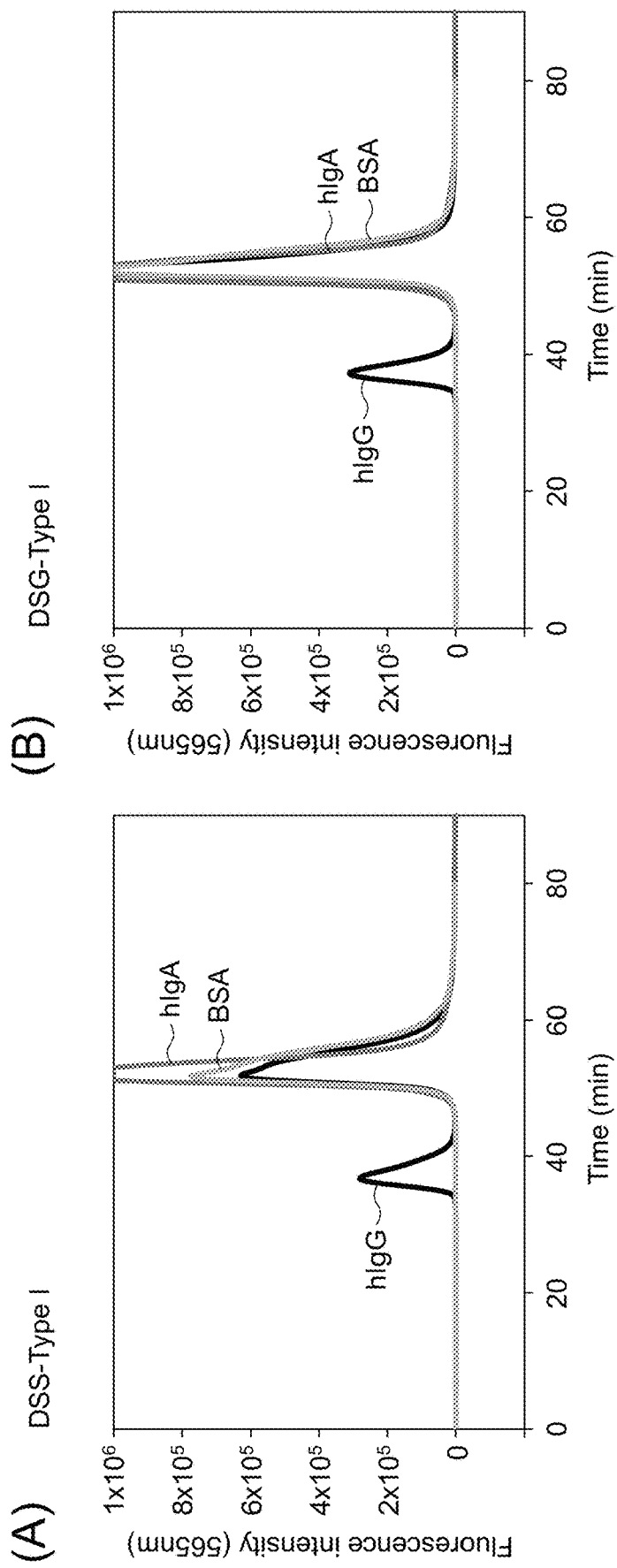
FIG. 4 shows results of measuring the reactivity of a labeled IgG-binding peptide with each protein (hIgA, hIgG, and BSA (bovine serum albumin)) by use of size exclusion chromatography.

The labeled IgG-binding peptide reacted with DSS or DSG was reacted with each protein at a molar ratio of 1:5 to the protein at room temperature for 60 minutes, and analyzed by size exclusion chromatography. Use of the labeled IgG-binding peptides (DSS or DSG) exhibited the specificity of reactivity with IgG at the same level in both cases. The fluorescent labeling of other proteins such as hIgA and BSA was not detected (FIG. 4). These results demonstrated that human IgG can be fluorescently labeled with high specificity using any of the prepared IgG-binding peptides.

Example 6: Analysis of Fc Modified with IgG-Binding Peptide (pH 4.5)

<Method>

An IgG-binding peptide (RGNCAYHXGQLVWCTYH (SEQ ID NO: 35), wherein X represents lysine) (4 mM) modified with DSG in the same way as in Example 2, dissolved in DMF was added in an amount of 0.5, 1.0, 2.0, or 5.0 μL (molar ratio: 0.5, 1.0, 2.0, or 5.0) to 200 μL of a human IgG (Chugai Pharmaceutical Co., Ltd.) Fc solution (20 μM, 0.1 M acetate buffer solution, pH 4.5), and the mixture was rapidly stirred and then reacted at room temperature for 15 minutes. The reaction was terminated by the addition of 10 μL of 1 M Tris-HCl (pH 7.0). 50 μL of the reaction product was injected to NGC Chromatography system (Bio-Rad Laboratories, Inc.) connected with Shodex IEC SP-825 column, followed by gradient elution from a 25 mM acetate buffer (pH 4.5) to a 25 mM acetate buffer (pH 4.5) containing 1 M NaCl. The protein elution was monitored on the basis of absorbance at 215 nm. Each obtained peak was separated and subjected to molecular weight measurement by LC/MS.

20 μL of the obtained fraction of the peak was injected to Shimadzu LCMS-8030 connected with Waters ACQUITY UPLC BEH C8 (1.7 μm, 2.1 mm×100 mm) column, followed by gradient elution from 4% acetonitrile containing 0.1% formic acid to 60% acetonitrile containing 0.1% formic acid. The eluted peaks were subjected to mass spectrometry, and the masses were calculated by deconvolution from polyvalent ion peaks using analytical software.
<Results>

Figure 5:
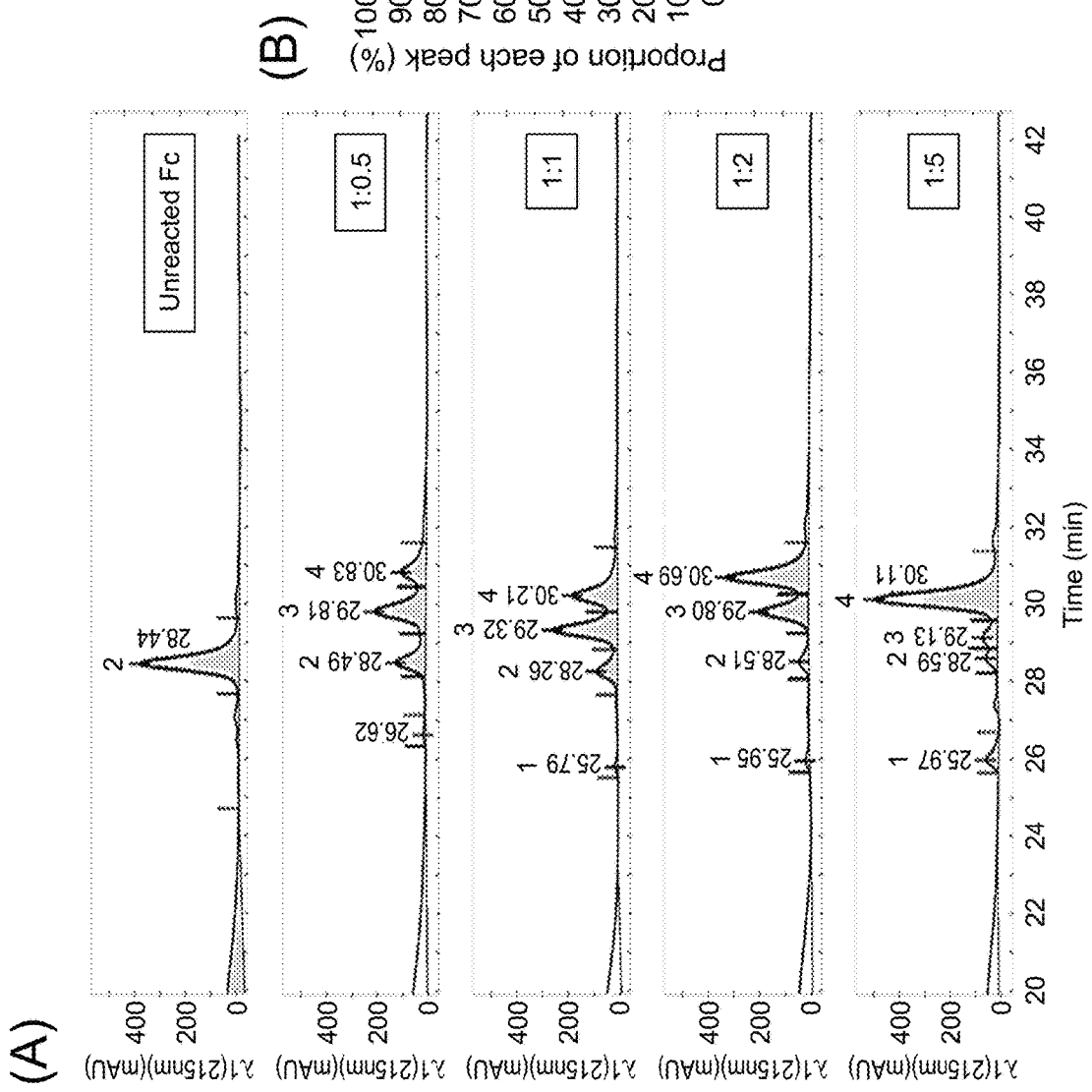
FIG. 5(A) shows results of liquid chromatography after adding a DSG-modified IgG-binding peptide dissolved in DMF to a human IgG Fc solution at a molar ratio of 0.5, 1.0, 2.0, or 5.0, stirring the mixture, and then allowing them to react at room temperature.
FIG. 5(B) shows change in the amounts of production of an unreacted form (peak 2), an adduct of one peptide (peak 3), and an adduct of two peptides (peak 4) when human IgG and a DSG-modified IgG-binding peptide were reacted at each molar ratio.

The DSG-modified IgG-binding peptide (4 mM, Biotin-PEG4-RGNCAYHXGQLVWCTYH-NH$_2$ (SEQ ID NO: 35); molecular weight: 2760, wherein X represents DSG-modified lysine, and the two Cys residues formed an intramolecular SS bond) was reacted at a molar ratio of 0.5, 1.0, 2.0, or 5.0 with human IgG1 Fc. As a result, as shown in FIG. 5A, a peak at the original elution position of human IgG1 Fc (peak 2) and two peaks (peaks 3 and 4) appeared (peak 1 seemed to be derived from the DSG-modified IgG-binding peptide). In order to identify these molecular species, LCMS analysis was conducted. IgG1 Fc before the reaction was eluted at peak 1 in an ion-exchange chromatogram and produced a value of 55084 in LCMS analysis. As a result of conducting the LCMS analysis of peaks 2, 3, and 4 after the reaction, values of 55087, 57735 (55087+2648), and 60384 (55087+5297), respectively, were obtained. This demonstrated that peak 2 after the reaction was derived from unreacted Fc, and peaks 3 and 4 were derived from Fc bound with one peptide and tow peptides, respectively.

FIG. 5B is a graph showing change in the amounts of production of the unreacted form (peak 2), the adduct of one peptide (peak 3), and the adduct of two peptides (peak 4) in reaction at each molar ratio. For example, even the reaction at a molar ratio of 1:1 produced 20% or less of the unreacted form, and the reaction at a molar ratio of 1:2 produced 10% or less of the unreacted form, demonstrating very high yields. Even at an excessive molar ratio of 1:5, the production ratio of the adduct of two peptides was relatively increased, whereas Fc with a larger number of peptides added thereto was not detected on an ion-exchange chromatogram, demonstrating that this labeling reaction is very specific.

Example 7: Influence of pH and Reaction Time on Reaction of Fc with IgG-Binding Peptide <Method>

1.0 µL (molar ratio: 1.0) of the DSG-modified IgG-binding peptide (4 mM) dissolved in DMF, prepared in Example 5 was added to 200 µL of a human IgG Fc solution prepared at pH 4.0 (25 mM acetate buffer solution), pH 5.5 (25 mM acetate buffer solution), or pH 7.0 (PBS), and the mixture was rapidly stirred and then reacted at room temperature. 1, 5, 10, or 30 minutes after the start of the reaction, the reaction was terminated by the addition of 10 µL of 1 M Tris-HCl (pH 7.0). 50 µL of the reaction product was injected to NGC Chromatography system (Bio-Rad Laboratories, Inc.) connected with Shodex IEC SP-825 column, followed by gradient elution from a 25 mM acetate buffer (pH 4.5) to a 25 mM acetate buffer (pH 4.5) containing 1 M NaCl. The protein elution was monitored on the basis of absorbance at 215 nm. On the basis of the obtained chromatogram, the percentage of each peak was calculated.
<Results>

Figure 6:
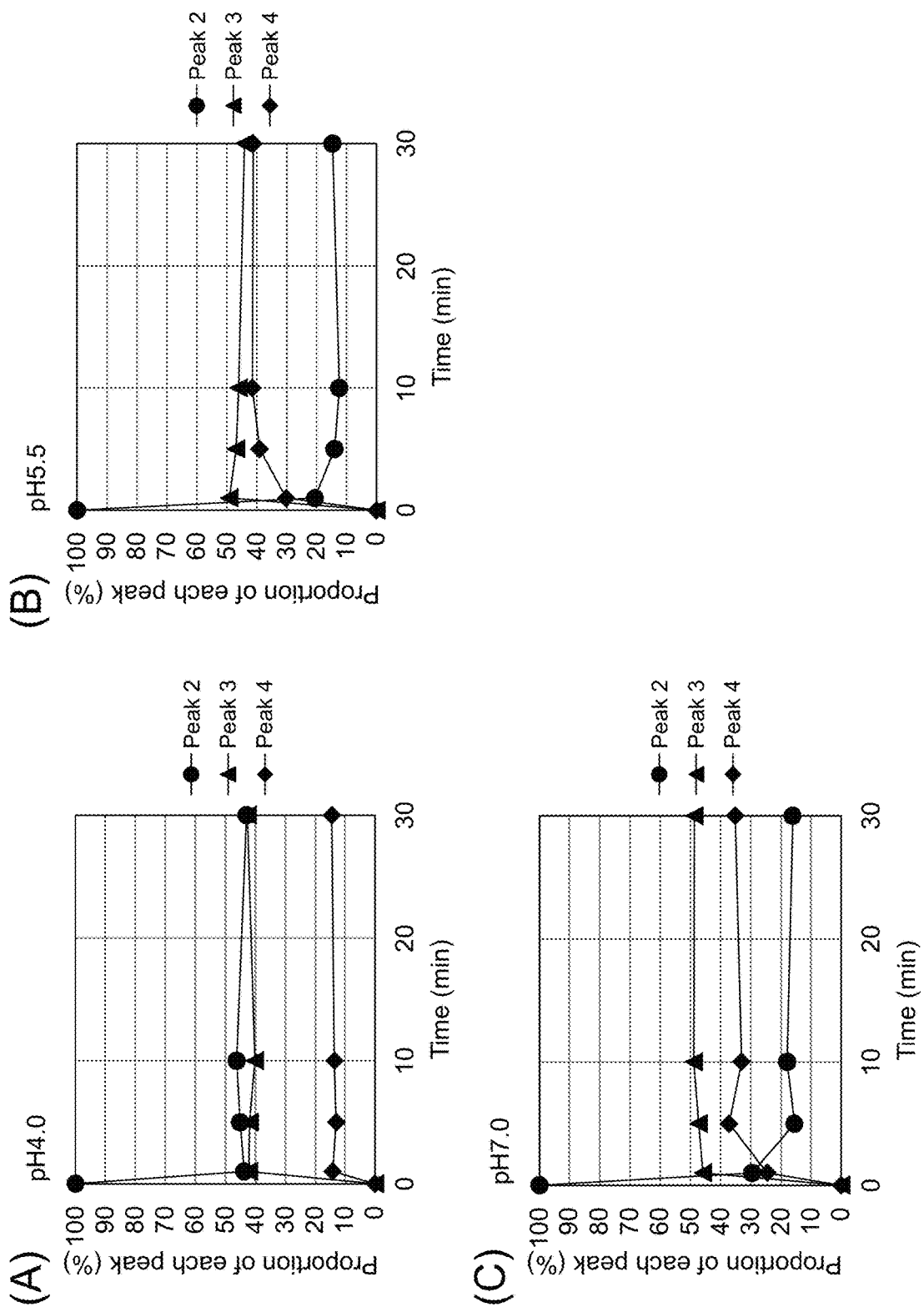
FIG. 6 shows change in the amounts of production of an unreacted form (peak 2), an adduct of one peptide (peak 3), and an adduct of two peptides (peak 4) 1, 5, 10, or 30 minutes after adding a DSG-modified IgG-binding peptide dissolved in DMF at a molar ratio of 1.0 to a human IgG Fc solution prepared at pH 4.0 (A), pH 5.5 (B), or pH 7.0 (C), stirring the mixture, and then allowing them to react at room temperature.

As shown in FIG. 6, labeling reaction proceeded rapidly at all of pH 4.0, pH 5.5, and pH 7.0 tested, demonstrating that 90% or more of the reaction completed within 1 minute. At pH 4.0, the amount of the unreacted form remaining exceeded 40%, and the reaction yield was low. Particularly, the yield of the adduct of two peptides (peak 4) was approximately 15% and was low as compared with other pH cases (35-40%). At pH 5.5 and 7.0, the yield of the unreacted form was also as low as the 10% level, demonstrating efficient reaction. As for the difference between pH 5.5 and 7.0, a tendency to slightly decrease the yield of peak 4 was seen at pH 7.0.

Example 8: Labeling of IgG-Binding Peptide with Radioactive Metal Nuclide and Detection of Cancer Using the Same—1

1) Preparation of DTPA-Containing IgG-Binding Peptide

An amino-PEG4-added IgG-binding peptide GPD-CAYHKGELVWCTFH (SEQ ID NO: 37, wherein two Cys residues formed an intramolecular SS bond, and the C terminus was amidated) with the N-terminal amino group modified with DTPA-tetra(tBu)ester (manufactured by CheMatech) was synthesized according to a routine method by the Fmoc solid-phase synthesis method. After deprotection, the purified DTPA-IgG-binding peptide was dissolved in 20 µL (19 mM) of DMSO. To the peptide solution, 20 µL of DSG (500 mM) dissolved in acetonitrile and 0.2 µL of pyridine (final concentration: 0.5%) were added, and the mixture was reacted at 50° C. for 3 hours. The whole amount was diluted with 10 ml of 15% acetonitrile containing 0.1% TFA and centrifuged. Then, the supernatant was injected to InertSustain® C18 column (7.6 mm 1×250 mm, GL Sciences Inc.), followed by elution in a gradient of 15% to 80% acetonitrile containing 0.1% TFA. The eluate was subjected to mass spectrometry, and the substance of interest (DSG-modified DTPA-PEG4-added IgG-binding peptide) was collected. After solvent removal, the residue was freeze-dried.

2) Preparation of Radioactive Nuclide-Labeled Antibody "DTPA-Modified Trastuzumab" Comprising DTPA-Containing IgG-Binding Peptide Bound to Trastuzumab The DSG-modified DTPA-PEG4-added IgG-binding peptide prepared in the preceding section 1) was dissolved at a concentration of 5.0 mM in DMSO. 1.36 µL of this solution and 1 mL of anti-HER2 human antibody (trastuzumab) (Chugai Pharmaceutical Co., Ltd.) (6.8 µM) dissolved in a 10 mM acetate buffer solution (pH 5.5) were mixed and reacted at room temperature for 30 minutes (molar ratio between the peptide and the antibody=1:1). The DTPA-modified human antibody (antibody-drug conjugate, ADC) thus prepared was purified by gradient elution of 0 M to 0.5 M NaCl containing a 10 mM Tris-HCl buffer solution (pH 7.0) on an anion-exchange column Shodex QA825 (8.0 mm×75 mm, Shodex). Two peaks (peaks A and B) other than unreacted antibodies were taken and then desalted and concentrated by centrifugation at 3000 g on Vivaspin (10000 Da cutoff, Sartorius AG). The mass of the obtained sample was measured using MALDI-TOF-MAS autoflex speed TOF/TOF-KG (Bruker Daltonics). The mass of the peak A was increased by 2716 (theoretical value: 2722) as compared with the original anti-HER2 human antibody, and the mass of the peak B was increased by 5398 (theoretical value: 5444) as compared with the original anti-HER2 human antibody. Therefore, one DTPA-PEG4-added IgG-binding peptide (anti-HER2 antibody-DTPA*1) and two DTPA-PEG4-added IgG-binding peptides (anti-HER2 antibody-DTPA*2) were confirmed to be introduced therein, respectively.

3) $^{111}$In Labeling of DTPA-Modified Trastuzumab and Confirmation of Radiochemical Purity of [$^{111}$In]-Labeled DTPA-Modified Trastuzumab The DTPA-modified trastuzumab prepared in the preceding section 2) was accurately weighed with a micropipette and placed in an Eppendorf tube (capacity: 1.5 mL). An acetic acid (0.15 M)-ammonia buffer solution (pH 5.5)

containing 10 mM citric acid was added thereto. The whole amount of the DTPA-modified trastuzumab solution was extracted using Myjector and placed in a colorless glass vial (capacity: 15 mL). A [$^{111}$In]Cl$_3$ solution in the same amount as the whole amount of the DTPA-modified trastuzumab solution was extracted using Myjector and placed in the colorless glass vial, and the mixture was well mixed. The number of moles of the DTPA-modified trastuzumab was adjusted to 20 to 100 times that of [$^{111}$In]. This mixture was reacted at room temperature for 30 minutes. After the completion of reaction, the amount of radioactivity was measured using a radioisotope dose calibrator.

5 mL each of a 1 M citric acid solution and a 1 M trisodium citrate solution was accurately weighed using a micropipette and transferred to a 100 mL volumetric flask. The amount of the solution was accurately adjusted to 100 mL by the addition of pure water. 1 mL of a 1% EDTA solution was accurately weighed using a micropipette and transferred to the 100 mL volumetric flask obtained in step 1, and the mixture was well mixed. This mixed solution was used as a developing solvent (prepared in use). The developing solvent was placed in a development container until approximately 1 cm from the bottom of the container. 3 µL of a test substance was accurately weighed using a micropipette and added dropwise to an origin set to 2 cm from the lower end of filter paper. Immediately after the dropwise addition, the filter paper was dried. A solvent front was set to 10 cm from the origin and placed in the developing solvent such that the lower end was dipped in the developing solvent. The filter paper was dried immediately after the developing solvent reached the upper end of the solvent front. Radioactivity remaining in the filter paper was measured using a radio-thin-layer chromatography analyzer (conditions: counting time: 20 min, energy range: 125-285 keV, binning: 2), and the radiochemical purity [%] of the [$^{111}$In]-labeled DTPA-modified trastuzumab was calculated from the ratio of the peak area of the origin.

Table 2 shows results of studying labeling using two DTPA-modified trastuzumab antibodies modified with a different number of DTPA-bound peptides per trastuzumab molecule. As shown in Table 1, all the DTPA-modified trastuzumab antibodies were able to be labeled with $^{111}$In.

TABLE 2

| Sample name | The number of DTPA-bound peptides with which one trastuzumab molecule was modified | Amount of added radioactivity | Radiochemical purity |
|---|---|---|---|
| 1-I | 1 | 5.76 MBq | 79.12% |
| 2-I | 1 | 6.57 MBq | 18.99% |
| 1-II | 2 | 6.57 MBq | 93.99% |
| 2-II | 2 | 6.67 MBq | 97.94% |

4) Evaluation of Binding Ability and Specificity of $^{111}$In-Labeled Trastuzumab for HER2

A cell line SK-OV-3 with high expression of HER2 (human-derived ovary cancer cells) and a cell line MDA-MB-231 with low expression of HER2 (human-derived breast cancer cells) (both obtained from American Type Culture Collection) were each collected using a trypsin-EDTA mixed solution and adjusted to 1.5×10$^7$ cells/mL with a serum-free medium to prepare a cell suspension. 200 µL of the cell suspension was accurately weighed using a micropipette, placed in a microtube (capacity: 1.5 mL), and cooled on ice. The number of samples was 3 for each experiment.

The $^{111}$In-labeled trastuzumab prepared in the preceding section 3) was diluted with a serum-free medium and adjusted such that the radioactivity concentration was 10 to 200 kB q/mL.

500 µL of the serum-free medium containing the $^{111}$In-labeled trastuzumab with the adjusted radioactivity concentration was accurately weighed using a micropipette, added to the microtube containing the cell suspension, and well mixed with the cell suspension. This mixture was reacted for 1 hour on ice. After the completion of reaction, centrifugation (centrifugal acceleration: 5000 g, temperature: 4° C., time: 5 min) was performed in order to wash off $^{111}$In-labeled trastuzumab nonspecifically adhering to the cells of each line without the mediation of HER2, and the supernatant was removed using a micropipette. Then, the cells were resuspended by the addition of 1 mL of a cold phosphate buffer solution and centrifuged (centrifugal acceleration: 5000 g, temperature: 4° C., time: 5 min). This washing operation was repeated three times. Finally, the supernatant was completely removed using a micropipette such that only pellets remained.

500 µL of the serum-free medium containing the $^{111}$In-labeled trastuzumab was accurately weighed using a micropipette and placed in a plastic tube (capacity: 1.5 mL). A plastic tube alone was provided as a blank (used for measuring a background value in order to calculate a net value in the calculation expression given below). The number of samples was 3 for each experiment. The amount of radioactivity of each sample was measured using an auto-well gamma counter (measurement conditions: energy range: 111-252 keV, preset time: 60 sec). The rate of binding (%) of the [$^{111}$In]-labeled trastuzumab to the cells of each line was calculated according to the following calculation expression using the measurement value.

$$\text{Binding rate (\%)} = \frac{\text{Count value of the pellets}}{\text{Count value of the added serum-free medium containing the }[^{111}In]\text{-labeled trastuzumab}} \times 100 \qquad \text{[Expression 1]}$$

*All of the count values represent the net values (determined by subtracting the background value from the measurement value, followed by decay correction).

The results are shown in Table 3. All the [$^{111}$In]-labeled trastuzumab antibodies were confirmed to have the ability to bind to HER2 and specificity.

TABLE 3

| Sample name | Binding rate (%) (n = 3, mean ± SD) | |
|---|---|---|
| | SK-OV-3 | MDA-MB-231 |
| 1-I | 59.94 ± 1.94 | 3.03 ± 0.10 |
| 2-I | 76.68 ± 2.08 | 3.83 ± 0.59 |
| 1-II | 54.17 ± 1.63 | 2.68 ± 0.17 |
| 2-II | 80.00 ± 3.11 | 4.29 ± 0.50 |

5) Confirmation of Binding Ability and Specificity of [$^{111}$In]-Labeled Trastuzumab for HER2 in Tumor and Specificity Thereof by SPECT Imaging Analysis SK-OV-3 (cell line with high expression of HER2) and MDA-MB-231 (cell line with low expression of HER2) were transplanted to the right and left lower limbs of each mouse (BALB/c, nu/nu, 19 weeks old, female, n=1) to prepare a cancer-bearing model, which was then subjected to SPECT/CT imaging. The SPECT imaging employed two [$^{111}$In]-labeled trastuzumab antibodies (trastuzumab modified with one DTPA-bound peptide molecule or two DTPA-bound peptide molecules per trastuzumab molecule).

(Preparation of $^{111}$In-Labeled Trastuzumab)

The $^{111}$In-labeled trastuzumab used in the subsequent experiments was prepared by the method described in the preceding section "3) $^{111}$In labeling of DTPA-modified trastuzumab and confirmation of radiochemical purity of [$^{111}$In]-labeled DTPA-modified trastuzumab" and purified by the ultrafiltration method. The antibody having one DTPA molecule in one molecule was designated as [$^{111}$In]-labeled trastuzumab-1 and the antibody having two DTPA molecules in one molecule was designated as [$^{111}$In]-labeled trastuzumab-2.

(Preparation of Cancer-Bearing Model)

The cell line SK-OV-3 with high expression of HER2 was transplanted to the left lower limb of each BALB/c nu/nu nude mouse, and the cell line MDA-MB-231 with low expression of HER2 was transplanted to the right lower limb thereof to prepare a cancer-bearing model. The cells of these lines were transplanted to the same one individual. The nude mouse was purchased from Japan SLC, Inc., and six 6-week-old female mice were used. On the day of imaging, the tumor volume of each mouse was measured, and two models having a tumor volume appropriate for the imaging experiment were selected. The cancer cells of each line used in these mice were obtained from American Type Culture Collection.

(Spect/Ct Imaging)
(Spect Imaging)

13 weeks after the transplantation, the [$^{111}$In]-labeled trastuzumab-1 solution (3.83 MBq) or the [$^{111}$In]-labeled trastuzumab-2 (2.64 MBq) solution was administered to each model from the tail vein. From 4 hours after the administration, imaging was carried out using a SPECT/CT camera (product name: FX3000 Pre-Clinical Imaging System). Then, imaging was carried out at the time points of 24 hours and 48 hours after the administration.

(Ct Imaging)

CT imaging was carried out prior to the SPECT imaging in order to confirm that tumor tissues fell within the field of view of SPECT imaging at the same time. Each model was anesthetized with isoflurane, and then mounted to an animal bed with the anesthesia maintained. The model was placed in a CT apparatus, irradiated with X ray, and positioned such that its tumor was at the center in the field of view. The CT imaging was carried out under imaging conditions given below to obtain CT images (raw files) of tumor.

Project count: 200 views
Frames averaged: 1 frame/view
Detector binning: 2×2
X-ray tube current: Default (150 µA)
X-ray tube voltage: 60 kV
Exposure time: 230 ms
Magnification: 1.8

The obtained raw files were reconstituted using Trifoil Console (reconstitution conditions: Half Res), and the reconstituted images were further converted using image display software to prepare DICOM files. These files were read using image analysis software (product name: PMOD 3.6) so that the images were displayed and used in the subsequent analysis.

(SPECT/CT Image Analysis)

At each time point after the administration of the [$^{111}$In]-labeled trastuzumab-1 solution or the [$^{111}$In]-labeled trastuzumab-2 solution, merged images of SPECT and CT were prepared and displayed at the coronal plane.

Table 4 shows the details of the model used in the in vivo experiment and information on the administered [$^{111}$In]-labeled trastuzumab-1 and [$^{111}$In]-labeled trastuzumab-2.

TABLE 4

| Administered radioactive drug | [$^{111}$In]-labeled Trastuzumab-1 | [$^{111}$In]-labeled Trastuzumab-2 |
|---|---|---|
| The number of DTPA-bound peptides with which one trastuzumab molecule was modified | 1 | 2 |
| Animal (sex) | BALB/c nu/nu mouse (♀) | |
| Age | 19 weeks old | |
| Body weight | 17.60 g | 18.13 g |
| Tumor volume (SK-OV-3, cell line with high expression of HER2) | 873 mm$^3$✕ | 205 mm$^3$ |
| Tumor volume (MDA-MB-231, cell line with low expression of HER2) | 650 mm$^3$ | 133 mm$^3$ |
| Dose of administrated radioactivity | 3.83 MBq (liquid volume: 0.14 mL) | 2.64 MBq (liquid volume: 0.14 mL) |
| Radiochemical purity | 91.41% | 65.18% |

✕Ulcer was observed in the tumor mass.

The imaging conditions of SPECT are shown in Table 5, and the image reconstitution conditions are shown in Table 6.

TABLE 5

| Isotope | Indium-111, high energy |
|---|---|
| Collimator | MMP(Multiplexed Multi-Pinhole)16 |
| Radius of rotation (ROR) | 55 mm |
| Projective limit | 150 sec or 300 sec |
| Angle of rotation | 90 degrees |

TABLE 6

| Item | Numeric value and conditions |
|---|---|
| Smoothing | Middle |
| Resolution | Middle |
| Iteration | Middle |

After the SPECT/CT imaging, merged images of SPECT and CT were prepared and displayed at the coronal plane. The results of SPECT/CT imaging of the mouse to which [$^{111}$In]-labeled trastuzumab-1 or [$^{111}$In]-labeled trastuzumab-2 was administered are shown in FIGS. 7, 8 and 9.

Figure 7:
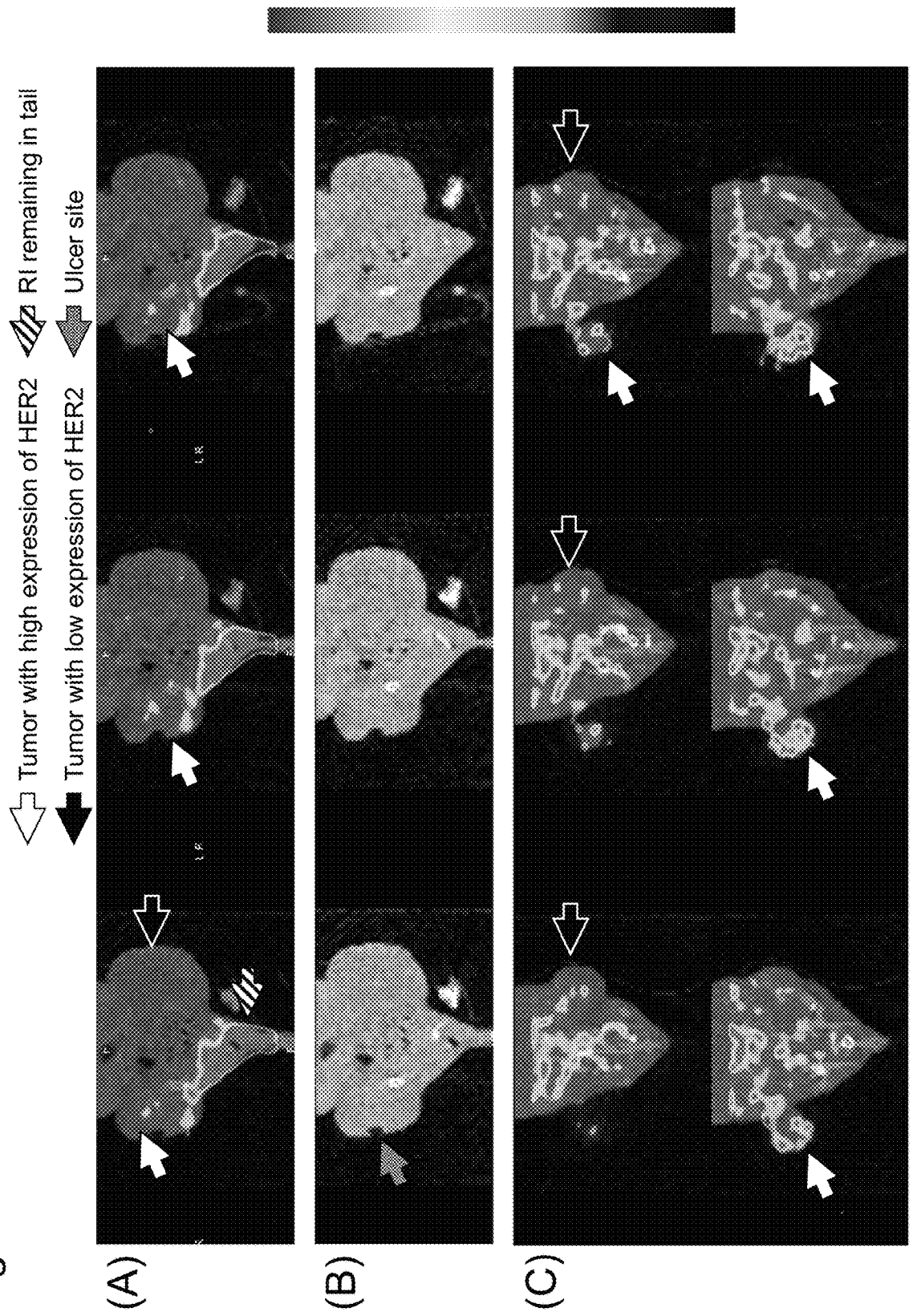
FIG. 7 shows SPECT/CT images (A) and CT images (B) including a tumor site 6 hours after administration of [$^{111}$In]-labeled trastuzumab-1, and SPECT/CT images (C) including a tumor site 4 hours after administration of [$^{111}$In]-labeled trastuzumab-2.

The SPECT/CT images taken 6 hours and 4 hours after the administration of [$^{111}$In]-labeled trastuzumab-1 and [$^{111}$In]-labeled trastuzumab-2, respectively, are shown in FIG. 7 as slice images including tumor. [$^{111}$In]-labeled trastuzumab-1 and [$^{111}$In]-labeled trastuzumab-2 were confirmed to accumulate in a tumor tissue with high expression of HER2, whereas their accumulation in a tumor tissue with low expression of HER2 was not observed. The nonspecific accumulation of [$^{111}$In]-labeled trastuzumab-1 in the tail was observed, but was due to the extravascular leakage of a portion of the solution at the time of administration.

Figure 8:
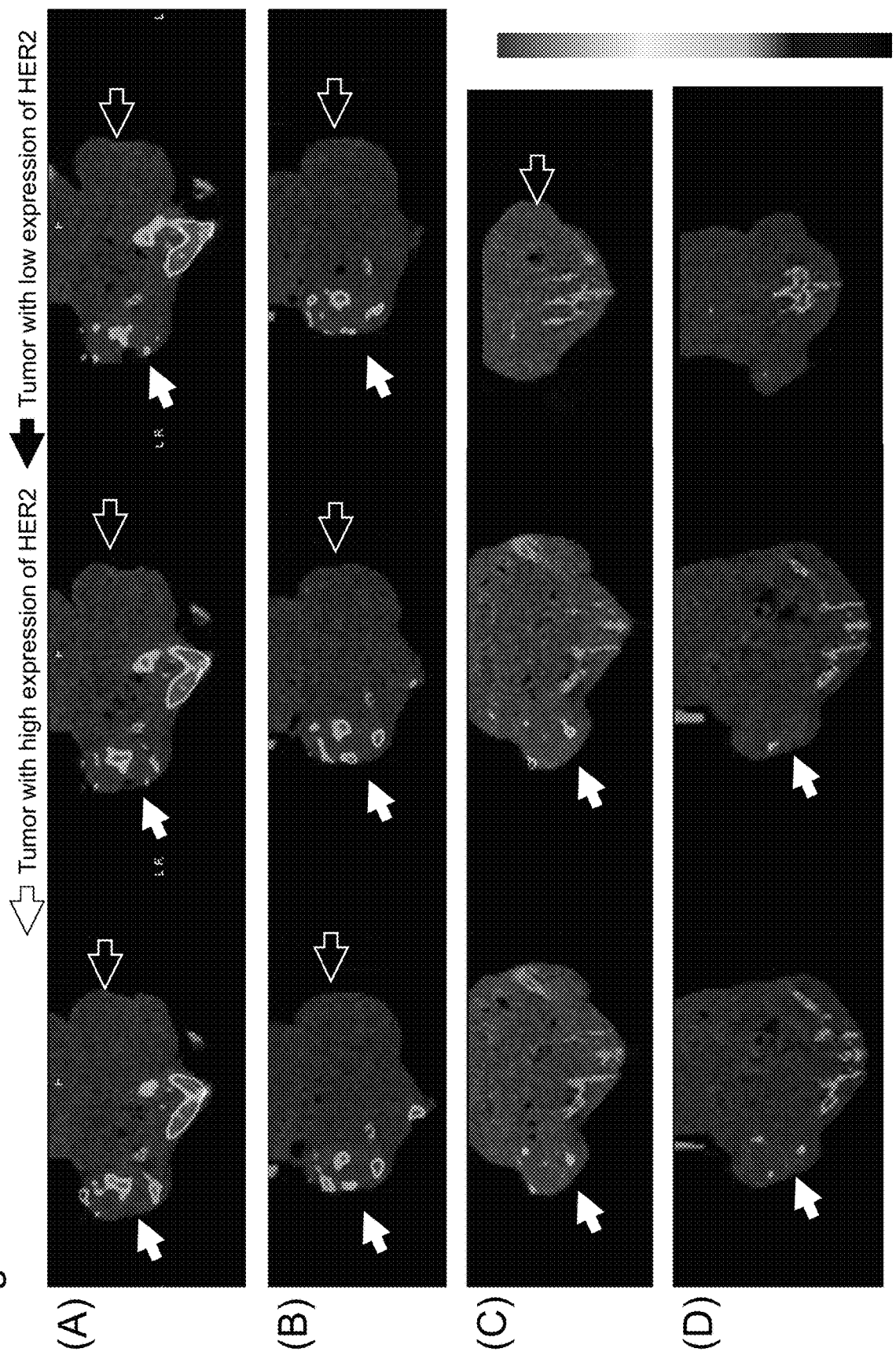
FIG. 8 shows SPECT/CT images including a tumor site 24 hours (A) and 48 hours (B) after administration of [$^{111}$In]-labeled trastuzumab-1, and SPECT/CT images including a tumor site 24 hours (C) and 48 hours (D) after administration of [$^{111}$In]-labeled trastuzumab-2.

The SPECT/CT images taken 24 hours and 48 hours after the administration of [$^{111}$In]-labeled trastuzumab-1 and [$^{111}$In]-labeled trastuzumab-2 are shown in FIG. 8 as slice images including tumor. The SPECT images were shown with scale values adjusted by decay correction carried out with reference to the time of imaging at the time point of 24 hours after the administration of [$^{111}$In]-labeled trastuzumab-1. [$^{111}$In]-labeled trastuzumab-1 and [$^{111}$In]-labeled trastuzumab-2 were confirmed to accumulate in a tumor tissue with high expression of HER2, whereas their accumulation in a tumor tissue with low expression of HER2 was not observed. The accumulation of [$^{111}$In]-labeled trastuzumab-1 to the tumor tissue with high expression of HER2 was higher than that of [$^{111}$In]-labeled trastuzumab-2 at all of the time points.

Figure 9:
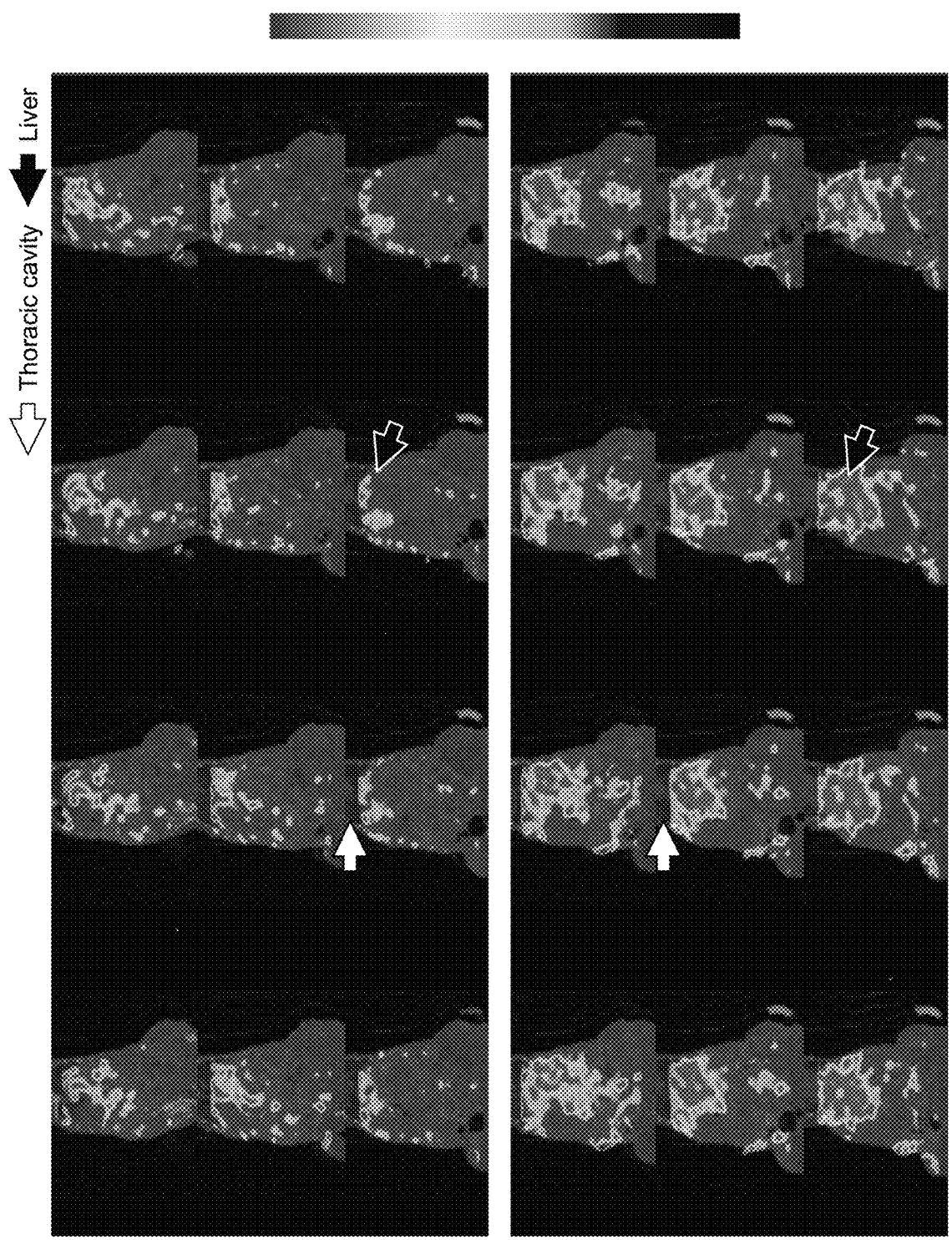
FIG. 9 shows SPECT/CT images including the liver 6 hours after administration of [$^{111}$In]-labeled trastuzumab-1 (A) and 4 hours after administration of [$^{111}$In]-labeled trastuzumab-2 (B).

The SPECT/CT images taken 6 hours and 4 hours after the administration of [$^{111}$In]-labeled trastuzumab-1 and [$^{111}$In]-labeled trastuzumab-2, respectively, are shown in FIG. 9 as slice images including the liver. The accumulation of [$^{111}$In]-labeled trastuzumab-2 to the liver at an early stage after the administration was higher than that of [$^{111}$In]-labeled trastuzumab-1. The position of the liver was determined from the thoracic cavity located thereabove.

Figure 10:
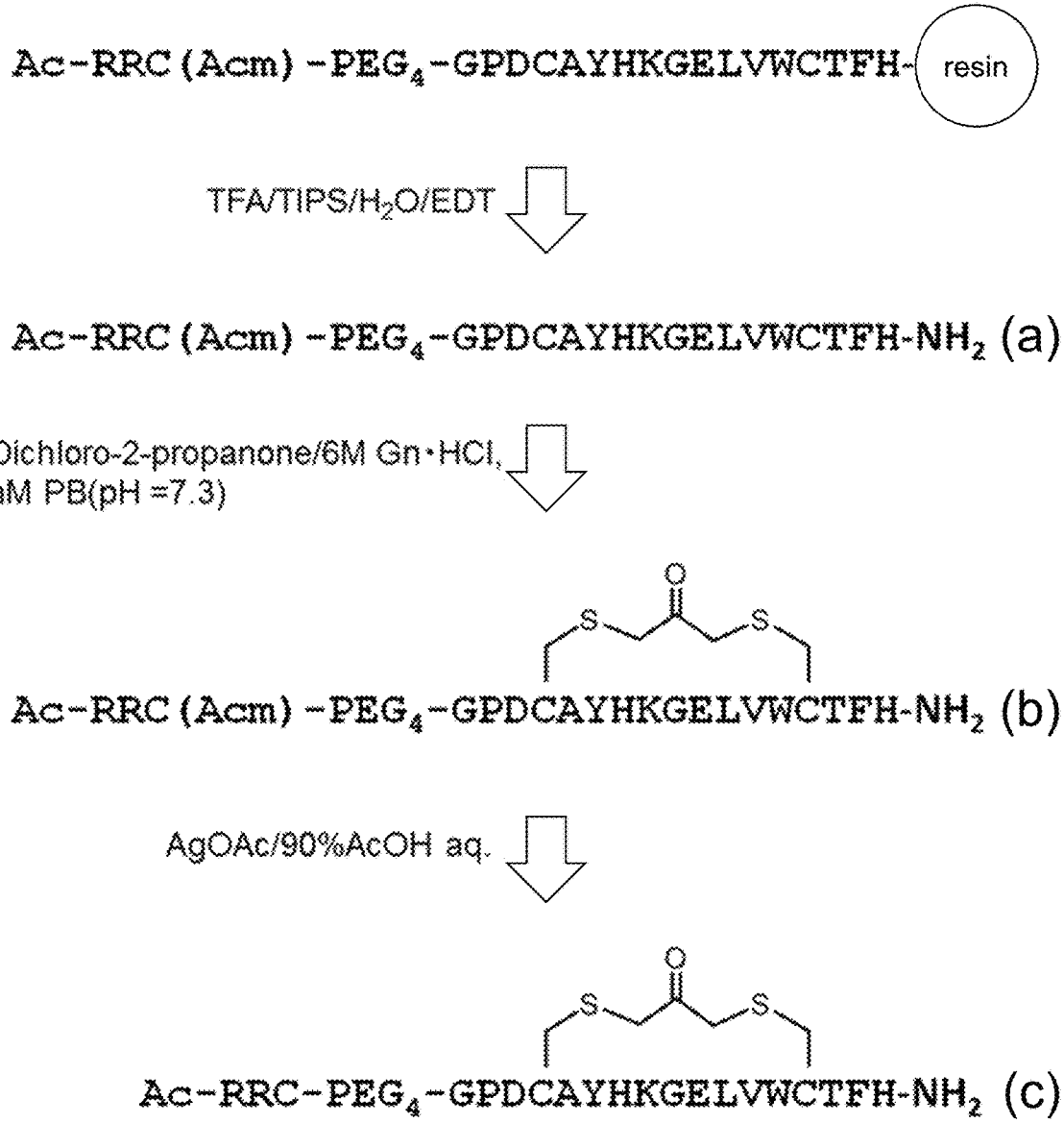
FIG. 10 shows a synthesis scheme of an IgG-binding peptide having a SS cross-linked structure via dichloropropanone, prepared in Example 9. Figure discloses "GPD-CAYHKGELVWCTFH" as SEQ ID NO: 37.

Example 9: Preparation of IgG-Binding Peptide Having SS Cross-Linked Structure Via Dichloropropanone An N-terminally acetylated RRC (Acm-protected)-PEG4-added synthetic peptide GPDCAYHXGELVWCTFH (SEQ ID NO: 2, wherein X represents lysine, and the C terminus was amidated) was synthesized according to a routine method by the Fmoc solid-phase synthesis method on peptide synthesis beads (Rink-amide-Chemmatrix resin, Biotage Japan, Ltd.). After excision of the peptide from the resin and deprotection, a peptide (FIG. 10, a) was obtained. 65 mg (15.6 µmol) of the obtained peptide was dissolved in 5 mL of a phosphate buffer solution (pH=7.3) containing 6 M Gn·HCl. 1,3-Dichloro-2-propanone (2.9 mg, 23.4 µmol, 1.5 molar equivalents) dissolved in 120 µL of acetonitrile was added thereto, and the mixture was stirred at room temperature. After 1 hour, the completion of the reaction was confirmed by HPLC analysis, and the reaction solution was directly purified by HPLC to obtain a cyclized peptide (FIG. 10, b, 33 mg, 7.8 µmol, yield: 50%). To this cyclized peptide, silver acetate (30.8 mg, 184.5 µmol) suspended in a 90% aqueous acetic acid solution (8.8 mL) was added, and the mixture was stirred at room temperature for 5 hours in the dark. Dithiothreitol (DTT; 352 mg, 2.3 µmol) was added thereto, and the resulting precipitates were removed by centrifugation. The obtained supernatant was purified by HPLC to obtain a cyclized peptide (FIG. 10, c, 20.5 mg, 5.2 µmol, yield: 67%).

Example 10: Labeling of IgG-Binding Peptide with Radioactive Metal Nuclide and Detection of Cancer Using the Same—2

<Method>
1) Preparation of Deferoxamine-Containing IgG-Binding Peptide

An amino-PEG4-added IgG-binding peptide GPD-CAYHKGELVWCTFH (SEQ ID NO: 37, wherein two Cys residues formed an intramolecular SS bond, and the C terminus was amidated) with the N-terminal amino group modified with deferoxamine-tetra(tBu) ester (manufactured by CheMatech) was synthesized according to a routine method by the Fmoc solid-phase synthesis method. After deprotection, the purified deferoxamine-IgG-binding peptide was dissolved in 40 µL (18 mM) of DMSO. To the peptide solution, 40 µL of DSG (500 mM) dissolved in acetonitrile and 0.5 µL of pyridine (final concentration: 0.6%) were added, and the mixture was reacted at 50° C. for 3 hours. The whole amount was diluted with 10 ml of 15% acetonitrile containing 0.1% TFA and centrifuged. Then, the supernatant was injected to InertSustain® C18 column (6.0× 250 mm, GL Sciences Inc.), followed by elution in a gradient of 10% to 66% acetonitrile containing 0.1% TFA. The eluate was subjected to mass spectrometry, and the substance of interest (DSG-modified deferoxamine-PEG4-added IgG-binding peptide) was collected. After solvent removal, the residue was freeze-dried.

2) Preparation of Radioactive Nuclide-Labeled Antibody "Deferoxamine-Modified Trastuzumab" Comprising Deferoxamine-Containing IgG-Binding Peptide Bound to Trastuzumab The DSG-modified deferoxamine-PEG4-added IgG-binding peptide prepared in the preceding section 1) was dissolved at a concentration of 13 mM in DMSO. 10 µL of this solution and 1 mL of anti-HER2 human antibody (trastuzumab) (Chugai Pharmaceutical Co., Ltd.) (22 µM) dissolved in a 10 mM acetate buffer solution (pH 5.5) were mixed and reacted at room temperature for 2 hours (molar ratio between the peptide and the antibody=6:1). The deferoxamine-modified human antibody (antibody-drug conjugate, ADC) thus prepared was purified by gradient elution of 0 M to 0.5 M NaCl containing a 10 mM Tris-HCl buffer solution (pH 7.0) on an anion-exchange column QA825 (8.0 mm×75 mm, Shodex). Two peaks (peaks A and B) other than unreacted antibodies were taken and then desalted and concentrated by centrifugation at 3000 g on Vivaspin® (10000 Da cutoff, Sartorius AG). The mass of the obtained sample was measured using MALDI-TOF-MAS autoflex speed TOF/TOF-KG (Bruker Daltonics). The mass of the peak A was increased by 2716 (theoretical value: 2722) as compared with the original anti-HER2 human antibody, and the mass of the peak B was increased by 5398 (theoretical value: 5444) as compared with the original anti-HER2 human antibody. Therefore, one deferoxamine-PEG4-added IgG-binding peptide and two deferoxamine-PEG4-added IgG-binding peptides were confirmed to be introduced in trastuzumab, respectively.

3) $^{89}$Zr-Labeling and Purification of Deferoxamine-Modified Trastuzumab $^{89}$Zr was dissolved at 200 MBq/200 µL in a 1 M oxalic acid solution. To a microtube, 200 µL of the $^{89}$Zr-oxalic acid solution and 90 µL of 2 M sodium carbonate were added, and the microtube was left at room temperature for 3 minutes. To the microtube thus left for 3 minutes, 1030 µL of a 0.5 M HEPES buffer solution (pH 7.1-7.3) containing 5 mg/mL gentisic acid was added with stirring. To 650 µL of this solution, 300 µL of the deferoxamine-modified trastuzumab (monovalent or divalent) prepared in the preceding section 2) was added, and the mixture was mixed. The reaction solution in the reaction vial was confirmed with pH test paper to have a pH of 6.8 to 7.2. After the pH confirmation, the reaction solution was reacted at room temperature for 1 hour. Then, the solvent in a PD-10 column was replaced with 20 mL of 0.25 M sodium acetate (pH 5.4-5.6) containing 5 mg/mL gentisic acid. Then, the $^{89}$Zr-labeled solution was applied to the PD-10 column (GE Healthcare Japan Corp.). 1.5 mL of 0.25 M sodium acetate (pH 5.4-5.6) containing 5 mg/mL gentisic acid was added thereto, and the eluate was discarded. 2 mL of 0.25 M sodium acetate (pH 5.4-5.6) containing 5 mg/mL gentisic acid was added thereto, and the eluate was fractionated into 0.2 mL each of fractions. Fractions having radioactivity were collected, followed by concentration operation using a centrifugal column for ultrafiltration (Amicon Ultra, manufactured by Merck Millipore). The $^{89}$Zr-labeled solution was developed on 50 mM EDTA (pH 5.0) as a developing solvent using a reverse-phase modified silica gel thin-layer chromatography (TLC) plate and TLC silica gel 60 RP-18 F254s (Merck Millipore). After the development, the TLC plate was exposed to an imaging plate (Fujifilm Corp.), and an autoradiogram was obtained using a fluoro image analyzer (FLA-7000, manufactured by GE Healthcare Japan Corp.). The radiochemical purity [%] of the [$^{89}$Zr]-labeled trastuzumab (monovalent or divalent) was calculated from the ratio of the peak area of the origin in the obtained autoradiogram.

4) Administration and PET Imaging of $^{89}$Zr-Labeled Trastuzumab

SK-OV-3 (cell line with high expression of HER2) and MDA-MB-231 (cell line with low expression of HER2) (both obtained from American Type Culture Collection) were transplanted to the right and left lower limbs of each mouse (BALB/c-nu/nu, female, 13 weeks old) to prepare a cancer-bearing model, which was then subjected to PET imaging. The PET imaging employed two [$^{89}$Zr]-labeled trastuzumab antibodies (trastuzumab modified with one deferoxamine-binding peptide molecule or two deferoxamine-binding peptide molecules per trastuzumab molecule) prepared according to the preceding section 3). The antibody having one deferoxamine molecule in one molecule was designated as [$^{89}$Zr]-labeled trastuzumab-1 and the antibody having two deferoxamine molecules in one molecule was designated as [$^{89}$Zr]-labeled trastuzumab-2.

The [$^{89}$Zr]-labeled trastuzumab-1 solution or the [$^{89}$Zr]-labeled trastuzumab-2 solution was administered to each model from the tail vein. From 6 hours after the administration, imaging was carried out using a PET camera (product name: Clairvivo® PET). Then, imaging was carried out at the time points of 24 hours and 48 hours after the administration. The 3D-DRAMA method was used as a method for reconstituting PET images.

Table 7 summarizes the details of the model used in the in vivo experiment and information on the administered [$^{89}$Zr]-labeled trastuzumab-1 and [$^{89}$Zr]-labeled trastuzumab-2.

TABLE 7

| Administered radioactive drug | [$^{89}$Zr]-labeled Trastuzumab-1 | [$^{89}$Zr]-labeled Trastuzumab-2 |
|---|---|---|
| The number of deferoxamine-bound peptides with which one trastuzumab molecule was modified | 1 | 2 |
| Animal (sex) | BALB/c nu/nu mouse (♀) | |
| Age | 13 weeks old | |
| Body weight | 18.8 g | 20.0 g |
| Tumor volume (SK-OV-3) | 150.8 mm$^3$ | 88.7 mm$^3$ |
| Tumor volume (MDA-MB-231) | 55.2 mm$^3$ | 116.2 mm$^3$ |
| Dose of administered radioactivity | 1.84 MBq | 4.28 MBq |
| Radiochemical purity | 100% | 100% |

Table 8 shows an imaging time at each time point. The imaging time at each time point was set, taking into consideration the dose of each labeled form and the decay of radioactivity.

TABLE 8

| | 6 hr | 24 hr | 48 hr |
|---|---|---|---|
| [$^{89}$Zr]-labeled Trastuzumab-1 | 30 min | 30 min | 60 min |
| [$^{89}$Zr]-labeled Trastuzumab-2 | 15 min | 15 min | 30 min |

<Results>

Figure 11:
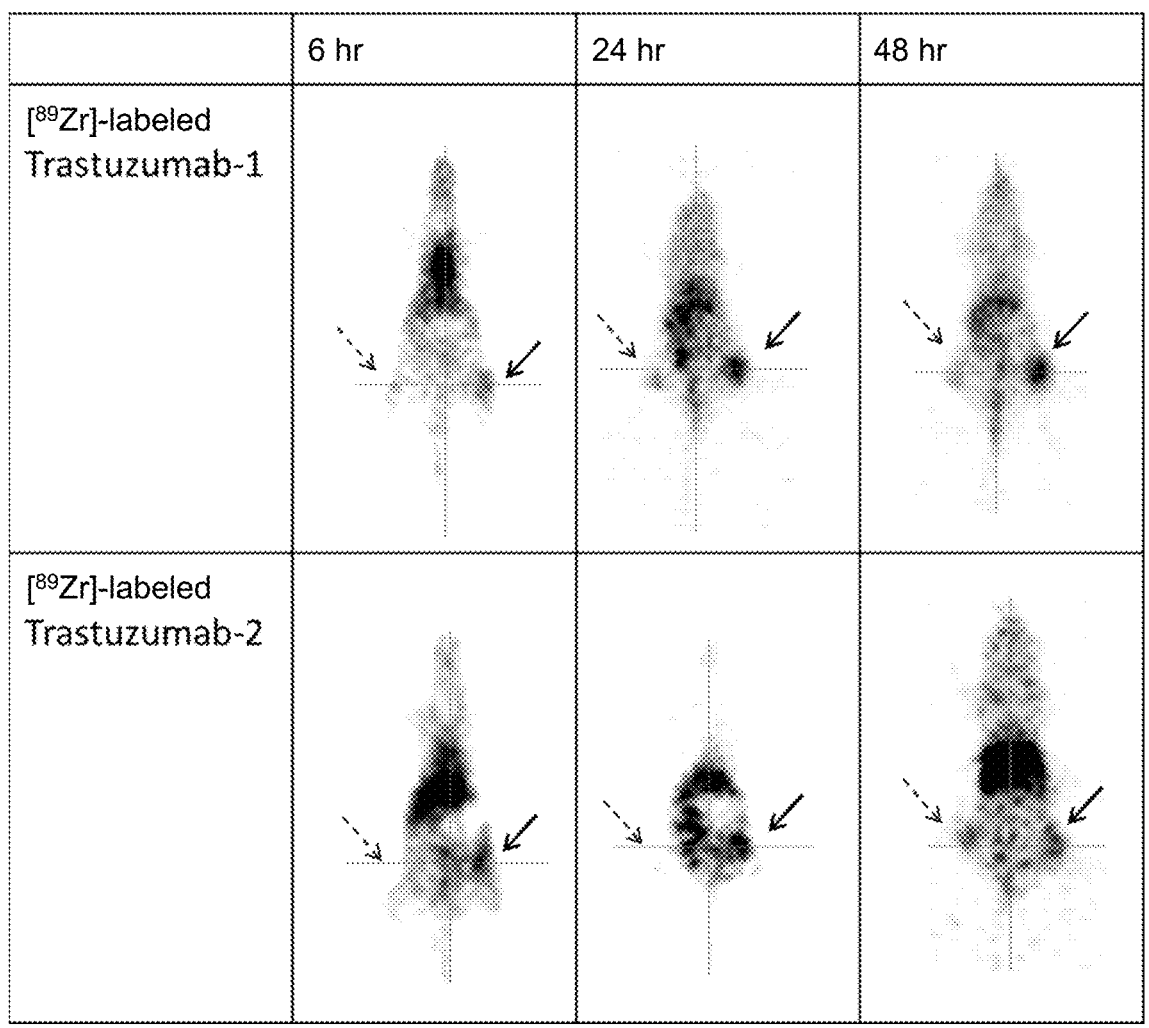
FIG. 11 shows PET images including a tumor site 6 hours, 24 hours, and 48 hours after administration of [$^{89}$Zr]-labeled trastuzumab-1 or -2. The solid line arrows depict a tumor tissue with high expression of HER2, and the broken line arrows depict a tumor tissue with low expression of HER2.

The PET images taken 6, 24 and 48 hours after the administration of each of [$^{89}$Zr]-labeled trastuzumab-1 and [$^{89}$Zr]-labeled trastuzumab-2 are shown in FIG. 11 as slice images including tumor. As shown in FIG. 11, [$^{89}$Zr]-labeled trastuzumab-1 and [$^{89}$Zr]-labeled trastuzumab-2 were confirmed to highly accumulate in a tumor tissue with high expression of HER2, as compared with a tumor tissue with low expression of HER2.

The IgG-binding peptide of the present invention can be easily bound to a radioactive metal nuclide. Therefore, IgG can be labeled specifically and conveniently with the radioactive metal nuclide without impairing the functions of the IgG. The IgG labeled with the radioactive metal nuclide can be used in the diagnosis of cancer.

All publications, patents and patent applications cited herein are incorporated herein by reference in their entirety.

The invention claimed is:

1. A peptide consisting of 13 to 17 amino acid residues represented by the following formula I:

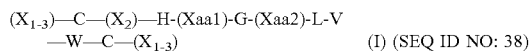 (I) (SEQ ID NO: 38)

wherein each X is independently any amino acid residue other than cysteine,

C is a cysteine residue,

H is a histidine residue,

Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue, a glutamine residue, or an asparagine residue, L is a leucine residue, V is a valine residue, and W is a tryptophan residue, wherein the peptide is capable of binding to human IgG, and wherein a ligand capable of binding to a radioactive metal nuclide is linked to the N terminus of the peptide, G is a glycine residue, Xaa2 is a glutamic acid residue, a glutamine residue, or an asparagine residue, L is a leucine residue, V is a valine residue, and W is a tryptophan residue, wherein the peptide is capable of binding to human IgG, and is labeled with a radioactive metal nuclide.

2. The peptide according to claim 1, wherein the radioactive metal nuclide is selected from the group consisting of $^{111}$In, $^{89}$Zr, $^{64}$Cu, $^{67/68}$Ga, and $^{99m}$Tc.

3. The peptide according to claim 1, wherein the ligand is a chelating agent.

4. The peptide according to claim 3, wherein the chelating agent is selected from the group consisting of diethylenetriaminepentaacetic acid (DTPA), deferoxamine, 1,4,7,10-tetraazacyclododecane-1,4,7,10-tetraacetic acid (DOTA), 1,4,7-triazacyclononane-1,4,7-triacetic acid (NOTA), and ethylenediaminetetraacetic acid (EDTA).

5. The peptide according to claim 1,
wherein the peptide consists of 13 to 17 amino acid residues represented by the following formula II:

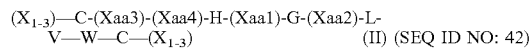 (II) (SEQ ID NO: 42)

wherein each X is independently any amino acid residue other than cysteine,

C is a cysteine residue,

H is a histidine residue,

Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue, a glutamine residue, or an asparagine residue, L is a leucine residue, V is a valine residue, W is a tryptophan residue, Xaa3 is an alanine residue, a serine residue or a threonine residue, and Xaa4 is a tyrosine residue or a tryptophan residue.

6. The peptide according to claim 1, wherein the peptide consists of 13 to 17 amino acid residues represented by the following formula I*:

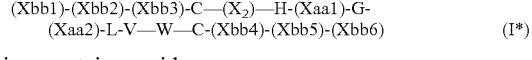 (I*)

C is a cysteine residue,

H is a histidine residue,

Xaa1 is a lysine residue, a cysteine residue, an aspartic acid residue, a glutamic acid residue, 2-aminosuberic acid, or diaminopropionic acid, G is a glycine residue, Xaa2 is a glutamic acid residue, a glutamine residue, or an asparagine residue, L is a leucine residue, V is a valine residue, W is a tryptophan residue, Xbb1 is S, G, F, R or none, Xbb2 is D, G, A, S, P, homocysteine, or none, Xbb3 is S, D, T, N, E or R, Xbb4 is S, T or D, Xbb5 is H, G, Y, T, N, D, F, homocysteine, or none, and Xbb6 is Y, F, H, M or none.

7. The peptide according to claim 1, wherein the peptide consists of GPDCAYHKGELVWCTFH (SEQ ID NO: 37), wherein the two Cys (C) residues form an intramolecular SS bond.

* * * * *

UNITED STATES PATENT AND TRADEMARK OFFICE
CERTIFICATE OF CORRECTION

PATENT NO. : 12,037,417 B2
APPLICATION NO. : 16/309272
DATED : July 16, 2024
INVENTOR(S) : Yuji Ito et al.

It is certified that error appears in the above-identified patent and that said Letters Patent is hereby corrected as shown below:

In the Claims

Column 65, Claim 1, Line 49, "and is labeled with a radioactive metal nuclide" should be --and wherein a ligand capable of binding to a radioactive metal nuclide is linked to the N terminus of the peptide--.

Signed and Sealed this
Twenty-ninth Day of October, 2024

Katherine Kelly Vidal
*Director of the United States Patent and Trademark Office*